(12) United States Patent
Matsumura

(10) Patent No.: US 9,144,413 B2
(45) Date of Patent: Sep. 29, 2015

(54) ULTRASONIC DIAGNOSTIC APPARATUS

(75) Inventor: Takeshi Matsumura, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 586 days.

(21) Appl. No.: 11/909,841

(22) PCT Filed: Mar. 30, 2006

(86) PCT No.: PCT/JP2006/306712
§ 371 (c)(1),
(2), (4) Date: Sep. 27, 2007

(87) PCT Pub. No.: WO2006/106852
PCT Pub. Date: Oct. 12, 2006

(65) Prior Publication Data
US 2009/0149750 A1    Jun. 11, 2009

(30) Foreign Application Priority Data

Mar. 30, 2005    (JP) .................................. 2005-097775

(51) Int. Cl.
A61B 8/00    (2006.01)
A61B 8/08    (2006.01)
A61B 5/00    (2006.01)
(Continued)

(52) U.S. Cl.
CPC ................. *A61B 8/08* (2013.01); *A61B 5/0048* (2013.01); *A61B 5/6843* (2013.01); *A61B 8/463* (2013.01); *A61B 8/485* (2013.01); *A61B 5/02007* (2013.01); *A61B 8/0825* (2013.01); *A61B 8/461* (2013.01); *A61B 2562/0247* (2013.01);

(Continued)

(58) Field of Classification Search
None
See application file for complete search history.

(56) References Cited

U.S. PATENT DOCUMENTS 5,203,337 A * 4/1993 Feldman ........................ 600/463
5,285,788 A * 2/1994 Arenson et al. ............... 600/441
(Continued)

FOREIGN PATENT DOCUMENTS

EP    1 421 905    5/2004
JP    5-115480    5/1993
(Continued)

OTHER PUBLICATIONS

Kanai, Hiroshi et al., Imaging of Elasticity Distribution in Arterial Wall by Transcutaneous Ultrasound and Electronic Staining, Rinsho Byori 51:305-812, Japan, Aug. 2003.
(Continued)

*Primary Examiner* — Nicholas Evoy
(74) *Attorney, Agent, or Firm* — Jones Robb PLLC

(57) ABSTRACT

The present invention provides an ultrasonic diagnostic apparatus that is capable of displaying an elastic image, enabling an accurate and easy identification of tissue characteristics of a diagnostic part. Elasticity data regarding a test object is obtained based on a received signal of an ultrasonic probe, and an elastic image representing a distribution of the elasticity data of the test object is generated. A display mode setting means sets a display mode of the elastic image in such a manner that a different tissue can be identified based on a value of the elasticity data. In this case, the display mode is differentiated by the value of the elasticity data within one tissue. With this configuration, the tissue characteristics of the diagnostic part are identified by the elasticity data, and displayed in a different display mode, thereby displaying an elastic image identifiable accurately and easily.

24 Claims, 15 Drawing Sheets

(51) Int. Cl.
  *G01S 15/89* (2006.01)
  *A61B 5/02* (2006.01)
  *G01S 7/52* (2006.01)

(52) U.S. Cl.
  CPC ...... *A61B 2562/043* (2013.01); *G01S 7/52071* (2013.01); *G01S 15/8979* (2013.01)

(56) References Cited

U.S. PATENT DOCUMENTS

| | | | |
|---|---|---|---|
| 5,687,737 A * | 11/1997 | Branham et al. | 600/523 |
| 5,961,460 A * | 10/1999 | Guracar et al. | 600/440 |
| 6,132,380 A * | 10/2000 | Cohen et al. | 600/481 |
| 6,135,957 A * | 10/2000 | Cohen-Bacrie et al. | 600/438 |
| 6,159,151 A * | 12/2000 | Bonnefous | 600/440 |
| 6,251,075 B1 * | 6/2001 | Hashimoto | 600/453 |
| 6,558,324 B1 * | 5/2003 | Von Behren et al. | 600/440 |
| 6,647,135 B2 * | 11/2003 | Bonnefous | 382/128 |
| 6,656,122 B2 * | 12/2003 | Davidson et al. | 600/454 |
| 6,716,172 B1 * | 4/2004 | Kerby et al. | 600/443 |
| 6,749,571 B2 * | 6/2004 | Varghese et al. | 600/450 |
| 7,901,357 B2 * | 3/2011 | Boctor et al. | 600/443 |
| 8,485,976 B2 * | 7/2013 | Iimura et al. | 600/443 |
| 8,608,659 B2 * | 12/2013 | Waki et al. | 600/437 |
| 8,684,931 B2 * | 4/2014 | Tanigawa et al. | 600/438 |
| 2004/0015079 A1 * | 1/2004 | Berger et al. | 600/437 |
| 2004/0059224 A1 * | 3/2004 | Varghese et al. | 600/450 |
| 2005/0124881 A1 * | 6/2005 | Kanai et al. | 600/437 |
| 2006/0052702 A1 * | 3/2006 | Matsumura et al. | 600/443 |
| 2007/0112267 A1 * | 5/2007 | Matsumura et al. | 600/437 |

FOREIGN PATENT DOCUMENTS

| | | |
|---|---|---|
| JP | 05-317313 | 12/1993 |
| JP | 06-245937 | 9/1994 |
| JP | 2004-135934 | 5/2004 |
| WO | WO 03/015635 A1 | 2/2003 |
| WO | WO 2004/110280 | 12/2004 |

OTHER PUBLICATIONS

Kanai et al "Electronic staining: elasticity imaging of atheroma with transcutaneous ultrasound", 2003 IEEE Ultrasonics Symposium Proceedings, Honolulu, Hawaii, Oct. 5, 2001; IEEE, US vol. 1, 5 Oct. 5, 2003, pp. 220-223.

Jun Inagaki et al "Construction of reference data for classification of elasticity images of alterial wall" Ultrasonics Symposium IEEE Montreal, Canada, Aug. 23-27, 2004, Piscataway, NJ, IEEE, vol. 3, Aug. 23, 2004, pp. 2161-2164.

* cited by examiner

FIG.2
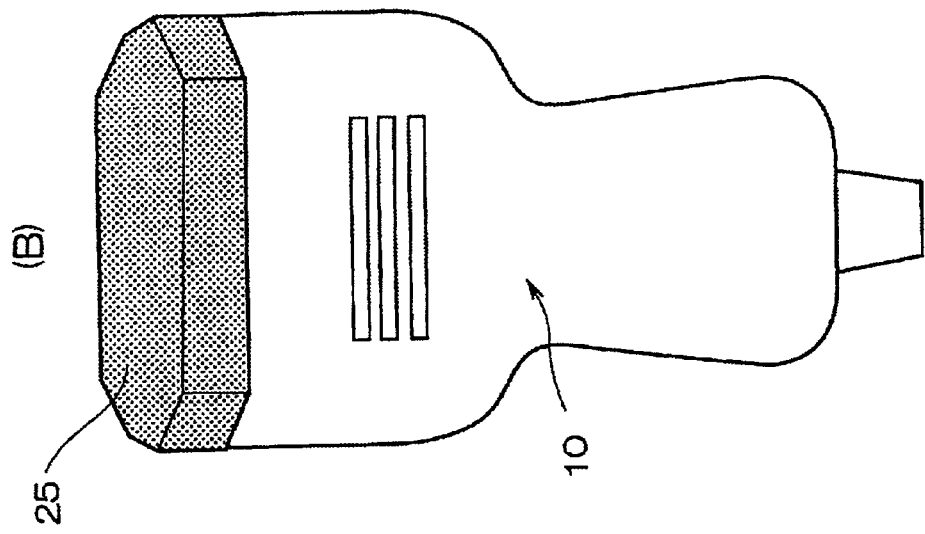
ULTRASONIC PROBE EQUIPPED WITH REFERENCE DEFORMABLE STRUCTURE
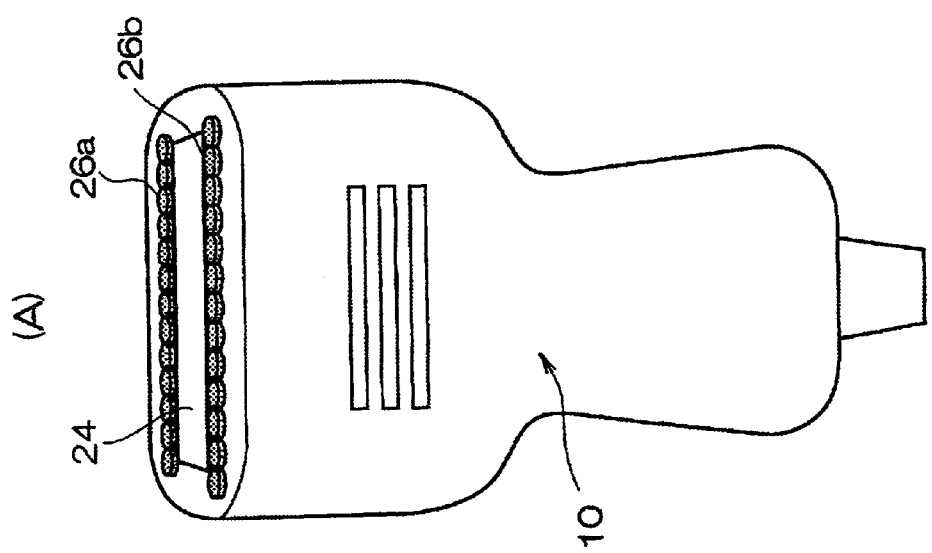
ULTRASONIC PROBE EQUIPPED WITH PRESSURE SENSOR FIG.15
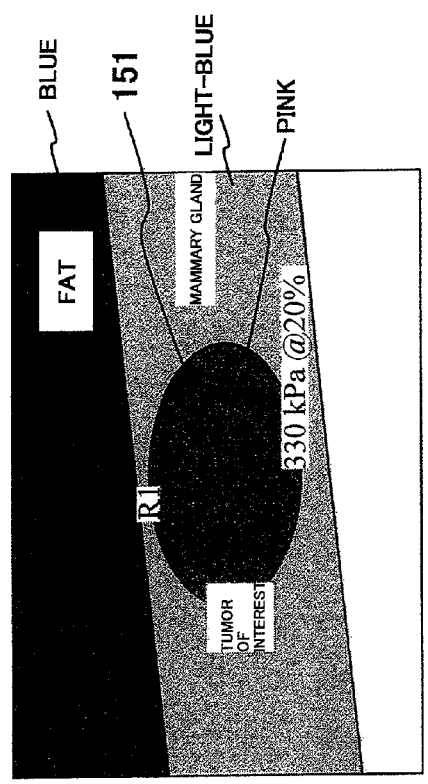
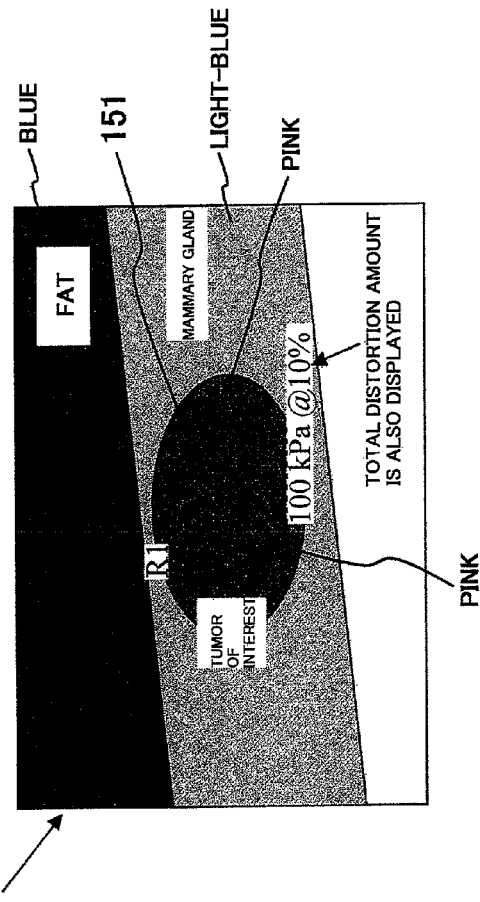

ULTRASONIC DIAGNOSTIC APPARATUS

TECHNICAL FIELD

The present invention relates to an ultrasonic diagnostic apparatus that reconfigures an elastic image, based on elasticity data, such as distortion and elastic modulus of a test object (subject to be examined).

BACKGROUND ART

An ultrasonic diagnostic apparatus which takes an image of a test object has conventionally displayed a structure of a living tissue of the test object, for example, in B-mode image. In recent years, the patent document 1, for instance, discloses an ultrasonic diagnostic apparatus that displays an elastic image that shows hardness and softness of the living tissue of the test object. As a method to generate the elastic image, the patent document 1 discloses that time-series images of the living tissue when a pressure is applied onto a diagnostic part are obtained, and correlates thus obtained time-series images to calculate a displacement and distortion of the living tissue, as well as measuring or estimating the pressure on the test object on the contact surface. According to the displacement and the pressure being calculated, elastic modulus of each of points on a tomographic image is obtained by an arithmetic computation, and the elastic modulus on each of the points configures an elastic image which shows a distribution of those points. Element data items of the elastic image being configured (elasticity data) are provided with hue information or monochrome brightness information according to a value of the elastic modulus, and these data items are displayed on a screen. With the configuration above, according to the hue of each part, it is possible to display an elastic image in which the elastic modulus level on each part can be identified.

Non-patent document 1 discloses that a mean value and a standard deviation of the elastic modulus are previously obtained, as to (a) lipid and (b) mixed composition of smooth muscle and collagen fiber, and then, points on the elastic image obtained in the ultrasonic diagnostic apparatus are classified into (a) lipid area, (b) mixed area of the smooth muscle and the collagen fiber, and (c) other tissue area. Then, each area is colored and displayed.

[Patent Document 1]
Japanese Published Unexamined Patent Application No. Hei05-317313
[Non-Patent Document 1]
Clinical Pathology 2003; 51: 8: 805-812

DISCLOSURE OF THE INVENTION

Problems to be Solved by the Invention

According to the technique disclosed in the patent document 1, it is possible to know from the elastic image, a level of hardness and softness of the living tissue. However, it is all left to a judgment of a laboratory personnel, how to interpret the level of hardness of the living tissue in the elastic image. In general, the hardness of the living tissue varies greatly, if the living tissue is different. The technique disclosed in the patent document 1 relates to a technique to separate the tissue by color, based on a difference in the elastic modulus with respect to each tissue. However, even in the case where the living tissue is the same, the hardness varies greatly depending on a property or a state of the tissue or a benignity or malignancy of the tissue (hereinafter, generally referred to as "tissue characteristics" as appropriate). Therefore, a result of judgment as to the tissue characteristics may be different depending on the amount of knowledge, experiences, and a skill level of the laboratory personnel. On the other hand, in the technique as disclosed in the non-patent document 1, separation by color based on the difference in the tissue characteristics is not considered, and there is a high possibility that if the tissue is the same, the color becomes the same. Therefore, with the technique as disclosed in the non-patent document 1, it is not easy to discriminate the tissue characteristics such as the tissue property and state, or benignity or malignancy thereof.

An object of the present invention is to provide an ultrasonic diagnostic apparatus that is capable of displaying an elastic image, which enables an accurate and easy identification of the tissue characteristics of a diagnostic part.

Means to Solve the Problem

In order to achieve the above object, the present invention provides an ultrasonic diagnostic apparatus as the following. That is, the ultrasonic diagnostic apparatus includes an ultrasonic probe for transmitting an ultrasonic wave to and receiving an ultrasonic wave from a test object, an elasticity data configuration means for obtaining elasticity data regarding the test object, based on a received signal of the ultrasonic probe, an image generation means for generating an elastic image showing a distribution of the elasticity data of the test object, and a display mode setting means for setting a display mode of the elastic image, in order that a different tissue becomes identifiable based on a value of the elasticity data, wherein, the display mode setting means sets different display modes within one tissue, corresponding to the value of the elasticity data thereof. With this configuration, a tissue characteristic of a diagnostic part can be identified by the elasticity data, and displayed in a different display mode. Therefore, an elastic image that is accurately and easily identifiable can be displayed.

A first aspect of the display mode setting means identifies degeneration states within one tissue according to the value of the elasticity data, and the display mode is differentiated in one tissue, corresponding to the degeneration state.

By way of example, the display mode setting means may have a color information imparting means that imparts color information differentiated by the degeneration state within one tissue. For this case, the color information may include a hue and brightness, and the color information imparting means has a configuration that at least one of the hue and the brightness varies continuously, according to the degeneration state in one tissue. It is further possible to configure such that the same hue is imparted to a denatured part within one tissue, and corresponding to the degeneration state on the denatured part, the brightness of the hue is continuously changed.

A second aspect of the display mode setting means may identify degeneration types within one tissue corresponding to the value of the elasticity data, and the display mode is differentiated by the degeneration type within one tissue. By way of example, the display mode setting means may have a color information imparting means that imparts color information as a display mode. A pattern, for instance, may be imparted as the display mode. Moreover, it is possible to impart numerical value information representing an elasticity property as the display mode.

The color information imparting means may divide a range of the elasticity data according to the degeneration type, and impart different color information items respectively to points in the one tissue, in association with the elasticity data range in which the elasticity data item of each of the points is included. Furthermore, the color information imparting means may separate, as a different elasticity data range, an area where the elasticity data ranges corresponding to at least two degeneration types are overlapping. In addition, the color information imparting means may impart the color information in such a manner that the color information discretely varies on the border between the elasticity data ranges.

It is possible for the color information imparting means to control imparting of the color information in such a manner that the same color information is assigned to the same degeneration type within one tissue. By way of example, the color information imparting means may prepare multiple types of elasticity data range in advance, and select the type of the elasticity data range so that the same color information is assigned to the same degeneration type.

In addition, the ultrasonic diagnostic apparatus according to the present invention may have a memory means for storing a value of the elasticity data for every degeneration type, with respect to each test object, and the color information imparting means defines the elasticity data range for every degeneration type, based on the multiple elasticity data items being stored in the memory means.

Furthermore, the aforementioned color information imparting means may have a storage unit for storing a map in which the elasticity data range is associated with the color information, and the color information may be imparted to each point of the image according to the map. In that case, the storage unit may store at least one map for each diagnostic part of the test object, and the color information imparting means is capable of selecting and using the map according to the diagnostic part of the test object. The map can be displayed in a form of color bar on the display means.

The color information imparted by the aforementioned color information imparting means may include at least one of the hue and the brightness. It is further possible for the color information imparting means to impart a different brightness according to the value of elasticity data, as to the point having the elasticity data within the elasticity data range to which the same hue is imparted.

In the present invention, the degeneration types may include at least one of the followings, for example; a cancer tissue, a thermally hardened tissue, a fibrous tissue, a tissue hardened by cooling, and a tissue softened by hormone therapy.

In the present invention, the elasticity data may be at least one of the followings, for example; elastic modulus, viscoelasticity ratio, distortion amount, viscosity, an amount of displacement, a stress, and Poisson's ratio.

In addition, the ultrasonic diagnostic apparatus according to the present invention may accept a setting of area of interest against the elastic image that is displayed on the display means, obtain statistical information about the elasticity data of each point within the area of interest, and display the statistical information in such a manner as associated with the elasticity data range on the color bar, or with the area of interest. It is further possible that a background area being separated by color just like the color bar is displayed on the display means, and a graph representing a temporal change of a mean value is displayed in such a manner as superimposing on the background area.

Effect of the Invention

According to the present invention, it is possible to implement the ultrasonic diagnostic apparatus that is suitable for displaying an elastic image in which tissue characteristics of the diagnostic part are accurately and easily identifiable. By way of example, it is possible to display an elastic image that is provided with numerical information representing color information, patterns, and elasticity properties, according to the type of tissue of the diagnostic part, and the type of the degeneration. In addition, it is further possible to display an elastic image in a different display mode depending upon the degree of the degeneration, even though the type of the degeneration is the same.

BEST MODE FOR CARRYING OUT THE INVENTION

One embodiment of the ultrasonic diagnostic apparatus to which the present invention is applied will be explained, with reference to the accompanying drawings. The ultrasonic diagnostic apparatus according to the present embodiment takes images and displays the images of both a grayscale tomographic image (monochrome tomographic image) of a test object, and an elastic image representing hardness or softness of the living tissue of the test object.

FIG. 1 is a block diagram showing a configuration of the ultrasonic diagnostic apparatus according to the present embodiment. As shown in FIG. 1, the ultrasonic diagnostic apparatus includes an ultrasonic probe 10 (hereinafter, referred to as "probe 10") for transmitting an ultrasonic wave to and receiving an ultrasonic wave from the test object 1, a transmitting circuit 12 as a sending means to supply a drive signal to the probe 10, a receiving circuit 13 and a phasing addition circuit 14 as receiving means to process a received signal outputted from the probe 10, an ultrasonic transmitting and receiving control circuit 30, a tomographic image generating system 101, and an elastic image generating system 102. The ultrasonic diagnostic apparatus further includes, a switch adder 44 for switching between the tomographic image and the elastic image, or adding one to the other, an image display 20, a cine memory 52, a device control interface 50, and a pressure measuring unit 27.

The elastic image generating system 102 includes an elasticity data construction unit 16, and a color scan converter 23. The elasticity data construction unit 16 obtains elasticity data of each point of the living tissue of the test object 1 according to a received signal outputted from the phasing addition circuit 14, and generates elastic frame data. The color scan converter 23 imparts different display mode information to element data (elasticity data) that constitutes the elastic frame data, and generates elastic image data showing a distribution of the elasticity data, according to an appropriate coordinate conversion process, or the like. The display mode information referred to here may include, in addition to the color information, pattern information for displaying a predetermined pattern in an area where the element data is displayed, and numerical value information that is imparted to represent the elastic property. Furthermore, the color information may include at least one of hue information and brightness information.

In the present embodiment, the color scan converter 23 identifies not only a type of the tissue, such as fat and mammary gland, but also tissue characteristics (degeneration information) based on elasticity data, and imparts information to display the parts having different type of tissues and degeneration information, respectively in different display modes. In other words, when the type of tissue and the types of degeneration (a cancer tissue, a thermally hardened tissue, a fibrous tissue, a tissue hardened by cooling, and a tissue softened by hormone therapy) are different, any of different color information items, pattern information items, numerical value information items representing the elasticity properties, and a combination of the information items are imparted. In addition, even when the type of tissue is the same or the type of degeneration is the same, if a degeneration state is different, this degeneration state is figured out according to the size of the elasticity data, and a different display mode is imparted. By way of example, if the degeneration state is different within the same tissue or within the tissue having the same degeneration type, at least one of the hue and the brightness is varied continuously.

The hue information, monochrome brightness information, and pattern information imparted by the type of tissue and by the type of degeneration, are previously defined in such a manner that the hue, the brightness, and the pattern vary discretely at the border between the types of tissue and the types of degeneration. The types of tissue and the types of degeneration are identified according to the value of elasticity data. Accordingly, it is possible to figure out the border between the different types of tissue or between the different tissue characteristics on the elastic image. Detailed configuration and operation of the color scan converter 23 will be described below.

It is to be noted that the elasticity data in the present embodiment represents numerical value data indicating an elasticity property and a property relating to the elasticity, regarding the living tissue of the test object 1, and includes at least one of elastic modulus (e.g., Young's modulus), viscoelasticity ratio, distortion amount, viscosity, amount of displacement, a stress, and Poisson's ratio. If two or more elasticity data items are employed, it is possible to generate different elastic images from the two data items, respectively. It is further possible that two or more images of elasticity data items are superimposed one on another and those images are displayed as one image. By way of example, if the Young's modulus and the viscoelasticity are displayed simultaneously as one image, it is utilized that one pixel of the elastic image is larger than one pixel of CRT and the like when being displayed, and adjacent two pixels of the elastic image are used as one pair. Then, images are displayed on the pixel on the left side in a display mode imparted based on the Young's modulus, and on the pixel on the right side in a display mode imparted based on the viscoelasticity. In the case above, by way of example, the hue of the Young's modulus may be rendered in five warm colors, and the hue of the viscoelasticity may be rendered in five cold colors, allowing both display modes to be distinguished. Accordingly, the elastic image is separated by color in a form of mosaic by pixel, and two elasticity data items can be displayed simultaneously.

Hereinafter, the ultrasonic diagnostic apparatus will be explained more in detail. FIG. 2 (A) and (B) show enlarged views of the ultrasonic probe 10 as shown in FIG. 1. As shown in FIG. 2, the probe 10 transmits an ultrasonic wave to and receives an ultrasonic wave from a test object, by way of mechanical or an electronic beam scanning. As shown in FIG. 2(A), multiple transducers are arranged on a plane facing the test object 1, and those transducers form a transducer group 24 in a shape of rectangular on the side of the ultrasonic wave sending and receiving surface. Each transducer is an element to transmit an ultrasonic wave directing to the test object 1, and receive a reflected echo generated from the test object 1 so that the echo is converted into a received signal. The probe 10 according to the present embodiment has a form to be brought into contact with a body surface of the test object 1. However, various forms may be applicable such as a transrectal probe, a transesophageal probe, an intraoperative probe, and an intravascular probe.

In addition, as shown in FIG. 2(A), the probe 10 has pressure sensors 26a and 26b being mounted on the periphery of the transducer group 24. By way of example, the pressure sensor 26a is disposed along one longitudinal line of the transducer group 24. The pressure sensor 26b is disposed along the other longitudinal line of the transducer group 24. Those pressure sensors 26a and 26b are connected to the pressure measuring unit 27 as shown in FIG. 1. The pressure measuring unit 27 is a meter that measures or estimates a pressure on the contact surface with the test object 1 based on detected values from the pressure sensors 26a and 26b, and then outputs the result as pressure data. It is to be noted here that the probe 10 is not limited to the form as shown in FIG. 2(A), and any form may be applicable as the probe 10, as far as it incorporates the transducer group 24, and it is also provided with a function to measure the pressure applied on the body surface of the test object 1. By way of example, as shown in FIG. 2(B), it is possible to employ a configuration in which a reference deformable structure 25 is mounted in such a manner as covering the transducer group 24 on the side facing the test object 1.

With the probe 10 as described above, an imaging method (Static Elastgraphy) is executed, which brings pressure on the test object 1, while an ultrasonic wave is sent to and received from the test object 1. As an operation to bring pressure, the ultrasonic wave sending and receiving surface of the probe 10 is brought into contact with the body surface of the test object 1, and the probe 10 is manually moved vertically to bring pressure (pressurization or depressurization) on the test object 1. However, the operation is not limited to the above example, and any mode for exerting pressure onto the test object 1 may be applicable.

On the other hand, in response to a command outputted from the ultrasonic transmitting and receiving control circuit 30, the transmitting circuit 12 generates a pulse signal as a drive signal and supplies the pulse signal being generated to the probe 10. In response to a command outputted from the ultrasonic transmitting and receiving control circuit 30, the receiving circuit 13 receives the received signal outputted from the probe 10, then subjects the signal to a process such as amplification, and outputs the processed signal to the phasing addition circuit 14. In the phasing addition circuit 14, phasing of the received signal outputted from the receiving circuit 13 is performed and it is added. It is to be noted here that the received signal outputted from the phasing addition circuit 14 is referred to as "RF signal".

In the subsequent stage of the phasing addition circuit 14, a tomographic image generating system 101 and an elastic image generating system 102 are arranged. The tomographic image generating system 101 includes a signal processor 34 and a monochrome scan converter 36. The signal processor 34 subjects the RF signal outputted from the phasing addition circuit 14 to a processing such as gain correction, log compression, detection, edge enhancement, and the like, and constructs tomographic image frame data. The monochrome scan converter 36 converts the tomographic image frame data outputted from the signal processor 34 into monochrome tomographic image data, and outputs the converted image to the switch adder 44.

The elastic image generating system 102 includes the elasticity data construction unit 16 and the color scan converter 23, as described above. As shown in FIG. 1, the elasticity data construction unit 16 is provided with an RF signal frame data selection unit 15, a displacement measuring unit 17, an elasticity data arithmetic unit 19, and an elasticity data processor 21. The RF signal frame data selection unit 15 stores the RF signals outputted in time-series from the phasing addition circuit 14, and selects a pair of RF signal frame data items. The displacement measuring unit 17 measures an amount of movement or displacement of the test object 1, being associated with each measuring point on the tomographic image, based on one pair of the RF frame data items outputted from the RF signal frame data selection unit 15, and generates displacement frame data. The elasticity data arithmetic unit 19 performs arithmetic computation of elasticity data of the test object 1, the elasticity data including at least one of the followings; elastic modulus (e.g., Young's modulus) viscoelasticity ratio, distortion amount, viscosity, amount of displacement, a stress, and Poisson's ratio, based on the displacement frame data outputted from the displacement measuring unit 17 and the pressure data outputted from the pressure measuring unit 27, and then, elastic frame data is generated. The elasticity data processor 21 subjects the elastic frame data outputted from the elasticity data arithmetic unit 19 to a predetermined signal processing.

The configuration and operation of each part of the elasticity data construction unit 16 will be further explained. The RF signal frame data selection unit 15 includes a frame memory for storing on a frame basis, multiple RF signals outputted from the phasing addition circuit 14, and a selection unit for selecting a pair of RF signal frame data items, i.e., two frame RF signal frame data items, from the frame memory. The RF signal frame data items are made up of a group of RF signals corresponding to one screen (a frame). By way of example, the RF signal frame data selection unit 15 sequentially reserves as the RF signal frame data, on a frame basis, the RF signals outputted in time-series from the phasing addition circuit 14. The RF signal frame data (N) is selected as a first data item, and also one RF signal frame data (X) is selected as a second data item from the RF signal frame data group (N-1, N-2, N-3, . . . N-M) having been reserved prior to the RF signal frame data (N). "N", "N", and "X" here indicate index numbers assigned to the RF signal frame data, and these are assumed as natural numbers.

The displacement measuring unit 17 subjects the first and the second RF signal frame data items being selected by the RF signal frame data selection unit 15 to a correlation processing, thereby measuring the displacement amount or displacement vector of each measuring point on the tomographic image, and outputting the results to the elasticity data arithmetic unit 19 as the displacement frame data. For example, the RF signal frame data (N) and the RF signal frame data (X) outputted from the RF signal frame data selection unit 15 are subjected to the correlation processing, and the displacement amount or the displacement vector are obtained. The correlation processing may be either of one-dimensional correlation and two-dimensional correlation. In addition, as a method for detecting the displacement vector, it is possible to apply a block matching method or a gradient method (see Japanese Published Unexamined Patent Application No. Hei 05-317313, for example). The block matching method is a processing which divides an image into blocks, for example, each made up of N×N pixels, and focuses attention on a block within an area of interest. Then, a block that is the closest to the focused block is found out from the previous frame, and referring to this block being found, a sample value is decided by a predictive coding, that is, by a difference between the blocks.

The elasticity data arithmetic unit 19 performs arithmetic computation of elasticity data of each measuring point on the tomographic image, the elasticity data including at least one of elastic modulus, viscoelasticity ratio, distortion amount, viscosity, an amount of displacement, a stress, and Poisson's ratio, based on the displacement frame data (e.g., displacement vector) outputted from the displacement measuring unit 17 and the pressure data outputted from the pressure measuring unit 27, and generates elastic frame data by bundling the computed elasticity data on frame basis. Then, the elastic frame data being generated is outputted to the elasticity data processor 21. By way of example, the distortion amount as one of the elasticity data does not need pressure data, and it can be obtained by the space derivative of the shift amount, e.g., displacement, of the living tissue. In addition, as shown in the following equation 1, the Young's modulus Ym as one of the elastic modulus is obtained by dividing the pressure (stress) by the distortion amount. Subscripts i and j in the equation 1 indicate each coordinate of the frame data.

$$Ym_{i,j} = \text{Pressure(Stress)}_{i,j} / \text{Distortion amount}_{i,j} \ (i, j = 1, 2, 3, \ldots)$$ (Equation 1)

Alternatively, the elastic modulus may be computed by using other parameters, such as stiffness parameter β, compressive elastic modulus Ep, and incremental elastic modulus Einc (see Japanese Published Unexamined Patent Application No. Hei 05-317313, for example).

The elasticity data processor 21 subjects the elastic frame data outputted from the elasticity data arithmetic unit 19 to the processing, such as a smoothing process within a plane of coordinate, contrast optimizing process, a smoothing process in the temporal axis direction, and outputs the processed data to the color scan converter 23.

The color scan converter 23 is provided with the functions as the following, the detailed structure thereof being shown in FIG. 3, a mapping function for imparting a display mode for displaying color information (at least one of the hue information and the monochrome brightness information) or pattern information, to element data (elasticity data) of the elastic frame data outputted from the elasticity data processor 21, and an outputting function for subjecting the elasticity data on which the mapping function is applied, to a predetermined coordinate converting process to output the processed data to the switch adder 44. Specifically, as shown in FIG. 3, the color scan converter 23 includes a memory circuit 46, a color information converter circuit 18, a coordinate converter circuit 48, and a discrimination map data storing unit 122, and implements the functions thereof.

The memory circuit 46 stores elastic frame data outputted from the elasticity data processor 21. The discrimination map data storing unit 122 previously stores discrimination map data 22. The color information converter circuit 18 follows the discrimination map data 22, and assigns at least one of the hue information and the monochrome brightness information to each of the elasticity data items of the elastic frame data read out from the memory circuit 46. The coordinate converter circuit 48 subjects the elastic frame data outputted from the color information converter circuit 18 to a predetermined coordinate conversion process, and outputs color elastic image data, i.e., hue information frame data, to the switch adder 44.

The discrimination map data 22 is a mapping function that is previously defined to assign the color information (at least one of the hue information and the brightness information) indicating a type of tissue and type of degeneration (tissue characteristics) corresponding to a value (intensity) of the elasticity data item as to the test object 1. The discrimination map data 22 will be detailed later. As for this discrimination map data 22, multiple data items are prepared in advance with respect to each diagnostic part of the test object 1, and one discrimination map data is selected in response to a control command.

In response to the control command, the coordinate converter circuit 48 subjects the elastic frame data outputted from the color information converter circuit 18 to an interpolation process for aspect ratio matching or a conversion process to a polar coordinate, for instance. Accordingly, an image having a coordinate relationship in conformity with the current measurement state is structured as color elastic image data. The color elastic image data being structured is outputted from the coordinate converter circuit 48 to the switch adder 44.

The switch adder 44 switches between the monochrome tomographic image data outputted from the monochrome scan converter 36 and the elastic image data outputted from the color scan converter 23, and either one of the data is displayed on the image display 20. Alternatively, the monochrome tomographic image data and the elastic image data may be added to one another to be outputted to the image display 20. By way of example, the switch adder 44 may select either one of the monochrome tomographic image and the color elastic image data to be displayed on the image display 20. Furthermore, both of the monochrome tomographic image data and the color elastic image data are selected to be simultaneously displayed side by side, according to the two-screen display function of the image display 20. Alternatively, the monochrome tomographic image data and the color elastic image data may be added to one another based on a predetermined weighting factor, and combined with one another, whereby a semitransparent superimposed image is generated and displayed on the image display 20. Accordingly, a diagnostic information as to the test object 1 can be displayed on the image display 20, thereby allowing a laboratory personnel to give a diagnosis referring to this image.

In addition, the switch adder 44 according to the present embodiment has a function to display on the image display 20, the discrimination map data 22 together with the color elastic image data, and a function to display on the image display 20, an indicator which indicates the tissue characteristic of the area of interest that is set on the color elastic image. By way of example, the switch adder 44 may display the discrimination map data 22 in a form of color bar, so as to figure out the correspondence between the elasticity data of the test object 1 and the hue information, and the correspondence between the type of tissue and the tissue characteristic, and the hue information or the brightness information. A specific display example will be explained in the embodiment 5 described below.

The device control interface 50 accepts a directive from the laboratory personnel, and generates a command to control the ultrasonic diagnostic apparatus in response to the directive. By way of example, the device control interface 50 outputs to the color scan converter 23, a command for selection from the discrimination map data 22, which is accepted from the laboratory personnel by an input means such as a keyboard. Furthermore, in response to an input command accepted from the laboratory personnel by the input means such as a mouse, a directive is outputted to the color scan converter 23 so as to set an area of interest on the color elastic image displayed on the image display 20.

An operation of the ultrasonic diagnostic apparatus configured as described above will be explained. Firstly, the ultrasonic wave transmitting and receiving side of the probe 10 is brought into contact, for example, with a body surface of the test object 1. In response to a command outputted from the ultrasonic transmitting and receiving control circuit 30, a drive signal is supplied from the transmitting circuit 12 to the probe 10 at a predetermined time interval. In response to the drive signal being provided, ultrasonic waves are transmitted to the test object 1 repeatedly from the probe 10. In the course of propagating within the test object 1, the ultrasonic wave is reflected as a reflected echo. The reflected echoes are sequentially transferred by the probe 10, and converted into received signals. The received signals being converted are processed as time-series RF signals by the receiving circuit 13 and the phasing addition circuit 14. The time-series RF signals being processed are outputted to both the signal processor 34 and to the RF signal frame data selection unit 15.

In transmitting the ultrasonic wave to and receiving the ultrasonic wave from the test object 1, the probe 10 is manually moved vertically with respect to the body surface of the test object 1. Accordingly, the test object 1 is pressurized or depressurized. The pressure applied to the test object 1 is measured by the pressure measuring unit 27 via the pressure sensors 26a and 26b.

According to the RF signals outputted from the phasing addition circuit 14, a monochrome tomographic image data is constructed by the signal processor 34 and the monochrome scan converter 36. The monochrome tomographic image data is displayed on the image display 20 via the switch adder 44, in response to the control command from the device control interface 50.

On the other hand, according to the RF signals outputted from the phasing addition circuit 14, displacement frame data is obtained by the RF signal frame data selection unit 15 and the displacement measuring unit 17, the displacement frame data being related to a shift amount or displacement of the test object 1, which is associated with each of the measured points on the tomographic image. According to the displacement frame data being obtained and the pressure data outputted from the pressure measuring unit 27, elastic frame data is reconstructed by the elasticity data arithmetic unit 19 and the elasticity data processor 21.

According to the discrimination map data 22, the elastic frame data outputted from the elasticity data processor 21 is provided with at least one of the hue information and the brightness information, by the color information converter circuit 18 of the color scan converter 23, with respect to each elasticity data that constitutes the elastic frame data. In other words, each of the elastic frame data is provided with either one of the hue information and the brightness information which are set in advance, with respect to each type of tissue and each type of the degeneration (tissue characteristic), in association with the size of the elasticity data regarding the test object 1. Accordingly, elastic image data is configured. The elastic image data is displayed on the image display 20 via the switch adder 44, in response to a control command from the device control interface 50.

According to the present embodiment, the discrimination map data 22 is structured as special map data, which divides the value of the elasticity data into multiple areas respectively corresponding to differences of the tissue types and degeneration types (tissue characteristic), and assigns at least one of different hue and brightness items to the areas, respectively. Therefore, when at least one of the hue information and the brightness information is assigned in conformity with the discrimination map data 22 by the color information converter circuit 18, to each elasticity data of the elastic frame data that is outputted from the elasticity data processor 21, the elastic frame data reflects the type of tissue or the type of degeneration estimated from the hardness of the diagnostic part, not reflecting the hardness itself. By displaying the elastic image corresponding to the elastic frame data on the image display 20, it is possible to identify from the image, the type of the tissue and the type of the degeneration of the diagnostic part, objectively and quantitatively. As a result, a diseased part or the like of a diagnostic tissue may be accurately and easily diagnosed, thereby enhancing the diagnostic efficiency and inspection accuracy.

Here, with reference to FIG. 4 to FIG. 8, embodiments and comparative examples of the discrimination map data 22 according to the present embodiment will be explained.

EMBODIMENT 1

As the embodiment 1, map data for mammary gland tissue 22a will be explained, with reference to FIG. 4. As for the map data for mammary gland tissue 22a, an elastic modulus is employed as the elasticity data, and the range of the elastic modulus is divided more than one, to be associated with types of breast tissue and tissue characteristics (types of degeneration). Then, different hue information items are assigned to the divided ranges, respectively. In other words, different hue information items are respectively assigned to the ranges of the elastic modulus corresponding to the fat, a mammary gland tissue, and fiber tissue, which are tissues without degeneration, and the ranges of the elastic modulus corresponding to mammary duct cancer and invasive infiltrating duct cancer as a mammary duct tissue having degeneration. In addition, since a range of the elastic modulus of the mammary duct cancer partially overlaps that of the fiber tissue, an alternative different hue is assigned to the overlapped range of the elastic modulus, so as to indicate that the overlapped range of the elastic modulus may be any one of the mammary duct cancer and the fiber tissue. Specifically, in the map data for mammary gland tissue 22a as shown in FIG. 4, the hues are assigned as the following, the fat is blue, the mammary gland tissue is light blue, the fiber tissue is green, a tissue having a possibility of any one of mammary duct cancer and fiber tissue is yellow, the mammary duct cancer is pink, and infiltrating duct cancer is red. However, it is possible to vary the hue as appropriate. In FIG. 4, the hue corresponding to each tissue is represented by various patterns for illustrative purpose. Further in FIG. 4, the patterns provided for respective tissues may be used substituting for the hues of the map data 22a. In this case, the patterns as shown in FIG. 4 are displayed for the respective tissues of an elastic image being identified.

In general, it is known that the hardness of the tissue varies greatly depending on its characteristic. By way of example, it is known that cancer becomes more solid along with the development of cancer, and palpation may be one of the methods that carry out a diagnosis according to a difference of the hardness. The ultrasonic diagnostic apparatus is conventionally able to generate an elastic image by obtaining the elastic modulus and the like by computation. However, it has been dependent on knowledge and experiences of the laboratory personnel to determine whether or not a tissue gets cancer, according to the hardness of the area of interest. By using the discrimination map data 22a of the present embodiment, each of the types of tissue (fat, mammary gland tissue, and fiber tissue) and each of two types of degeneration (mammary duct cancer and infiltrating duct cancer) can be associated with the elastic modulus in advance. With the configuration above, it is possible to display the types of tissue and the types of degeneration according to the hue, as objective information obtained from the elasticity data, without depending on the laboratory personnel's knowledge and experiences.

As thus described, when a color elastic image is displayed by applying the discrimination map data for mammary gland tissue 22a, the color elastic image becomes a tomographic image of breast separated by hue for each type of tissue and degeneration. Therefore, by referring to the color elastic image according to the present embodiment, it is possible to objectively identify the tissue characteristics of the mammary gland.

In addition, the chart 111 as shown in FIG. 4 indicates a previously obtained relationship between the types of tissue and degeneration in the mammary gland tissue, and the elastic modulus, so as to define the correspondence between the elastic modulus ranges and the hues in the color map data 22a. The vertical axis of the chart 111 indicates the elastic modulus, and the horizontal axis indicates the tissue characteristic. For the relationship described above, the one having been obtained in advance by experiments can be employed. Alternatively, it is possible to employ the information reported by Krouskop, et al. for example (T. A. Krouskop et al, Ultrasonic Imaging, 1998).

FIG. 4 also shows a conventional color map data 60 for comparison with the discrimination map data 22a of the present embodiment 1. As shown in FIG. 5, the hue information (blue, green, and red) that continuously varies in gradation according to the functions 62, 64, and 66 is assigned to the color map data 60 of the comparative example, in such a manner as associated with the value of the elasticity data only. By way of example, in FIG. 5, the colors from blue to green are assigned to the elastic modulus varying from 0 [kpa] to 400 [kPa], and the colors from green to red are assigned to the elastic modulus varying from 400 [kPa] to 800 [kPa].

In the color map data 60 of the comparative example as shown in FIG. 4, the area colored in blue-green extends over both the mammary duct cancer and the fiber tissue, and the gradation varies continuously thereon. Therefore, it is not possible to figure out the border between the mammary duct cancer and the fiber tissue (around 300 kPa and around 220 kPa of the elastic modulus). It is further impossible to figure out the range of elastic modulus (220 to 300 kPa) that may correspond to both the mammary duct cancer and the fiber tissue. Therefore, according to the image colored by blue-green, it is not possible to figure out whether or not there is a possibility of degeneration in the tissue. On the other hand, in the embodiment 1, the border between the mammary duct cancer the fiber tissue (around 300 kPa and around 220 kPa of the elastic modulus) can be clearly figured out, as the border between pink and yellow, and as the border between yellow and green. In addition, it is further possible to recognize as the color of yellow, the range of elastic modulus (from 220 to 300 kPa) that may indicate both the mammary duct cancer and the fiber tissue.

Similarly, when the color elastic image is displayed by the color map data 60 of the comparative example, it is difficult to identify whether a focused tissue associated with the green color of the elastic image indicates the mammary duct cancer or the infiltrating duct cancer. As for this point, according to the color elastic image obtained by the color map data 22a of the present embodiment 1, they are discriminated by the color, that is, the color red indicates the infiltrating duct cancer, and the color pink indicates the mammary duct cancer. With the color yellow, the area that has a possibility of both the mammary duct cancer and the fiber tissue can be identified.

EMBODIMENT 2

With reference to FIG. 6, the discrimination map data for mammary gland tissue 22b of another aspect will be explained as the embodiment 2. This discrimination map data 22b is the same as the map data 22a according to the embodiment 1, in the point that different hues are respectively assigned to the types of tissue and to the types of degeneration. However, in each hue, the brightness varies continuously within the hue in such a manner as associated with the magnitude of the elastic modulus. In other words, each of the hues indicating the types of tissue and existence of degeneration are respectively provided with the brightness continuously varying, to add gradations, and this point is different from the embodiment 1. By way of example, as for the infiltrating duct cancer, a higher-intensity (brighter) red is assigned, as the elastic modulus is increased, that is, as the state of degeneration is changed.

According to the map data 22b of the present embodiment 2, while identifying the types of mammary gland tissue and degeneration (mammary duct cancer, infiltrating duct cancer) by the difference in hues of the elastic image, the brightness of the hues can be visibly recognized. Therefore, it is possible to figure out the state of degeneration (degree of degeneration) and the magnitude of the elastic modulus. With the configuration above, the laboratory personnel is allowed to recognize the types of degeneration and the state of degeneration of the tissue (degree of degeneration), more specifically than the embodiment 1 where the discrimination map data 22a uses only the hues. Therefore, a diseased diagnostic tissue or the like may be accurately and easily diagnosed, thereby further enhancing the diagnostic efficiency and inspection accuracy. It is to be noted that another configuration may be possible such as varying the hue gradation continuously, instead of varying the brightness information.

EMBODIMENT 3

With reference to FIG. 7, the discrimination map data for mammary gland tissue 22c of another aspect will be explained as the embodiment 3. Unlike the map data 22a and 22b of the embodiments 1 and 2, in the discrimination map data for mammary gland tissue 22c, different hues are assigned depending on whether the mammary gland tissue is benign or malignant (whether or not the tissue is not denatured or denatured). In other words, as shown in FIG. 7, the color of red is assigned to the range of elastic modulus of the mammary duct cancer and the infiltrating duct cancer, the color of light-blue is assigned to the range of elastic modulus of the fat, mammary gland tissue, and fiber tissue, and the color of yellow is assigned to the range in which the elastic modulus of the mammary duct cancer overlaps that of the fiber tissue. By using the discrimination map data 22c as shown in FIG. 7, it is possible to directly and clearly recognize whether the elastic image is benign (light-blue) or malignant (red), or there is a possibility of both (yellow).

EMBODIMENT 4

The present invention can be applied not only to the mammary gland tissue but also any other target part. In the embodiment 4, with reference to FIG. 8, the discrimination map data for prostate tissue 22d will be explained by way of example. In the discrimination map data for prostate tissue 22d as shown in FIG. 8, the color of light blue is assigned to the range of elastic modulus of non-denatured tissue of prostate gland (anterior part of prostate and posterior part of prostate), the color of yellow is assigned to the range of elastic modulus of benign denatured tissue (prostatic hypertrophy), and the color of red is assigned to the range of elastic modulus of malignant denatured tissue (prostatic cancer). By applying this map data for prostate tissue 22d, it is possible to objectively discriminate the types of tissue and the types of degeneration (characteristic) of the prostate gland, according to the elastic modulus.

As described above, at least one type of the discrimination map data 22 can be prepared with respect to each diagnostic part, as described in the above embodiments 1 to 4. Therefore, it is possible to configure such that all of these data items are previously stored in the discrimination map data storing unit 122, and in response to the map data selection command accepted by the device control interface 50 from the laboratory personnel, one discrimination map data 22 item is selected and passed to the color scan converter 23.

By way of example, the discrimination map data items for mammary gland tissue 22a to 22c and the map data for prostate tissue 22d are previously stored in the discrimination data map storing unit 122, and when a mammary gland is diagnosed, one of the map data items for mammary gland tissue 22a to 22c appropriate for the diagnostic purpose is selected by the laboratory personnel. As a purpose of diagnosis, for example, if one wishes to know a mammary gland tissue structure and the type of degeneration, the discrimination map data 22a is selected. If one wishes to know the state of degeneration (degree of degeneration) in addition to the mammary gland tissue structure and existence of degeneration, the discrimination map data 22b is selected. If one wishes to know mainly the existence of degeneration, the discrimination map data 22c may be selected. When the prostate gland is diagnosed, the map data for prostate tissue 22d is selected. Accordingly, it is possible to impart a hue to the type of tissue and the type of degeneration (characteristic), in accordance with a property of hardness for each diagnostic part and a diagnostic purpose. Therefore, even when the tissue characteristics of multiple types of diagnostic parts are diagnosed, according to various diagnostic purposes, it is possible to identify the tissue characteristic of each diagnostic part, promptly and accurately.

EMBODIMENT 5

In the embodiments 1 to 4, various discrimination map data items 22a to 22d have been explained. In the embodiment 5, a displaying operation in displaying the elastic image using these discrimination map data items 22a to 22d, and a user interface such as a method for setting an area of interest will be explained.

As a display example of the embodiment 5, FIG. 9 shows an elastic image generated by using the map data for prostate tissue 22d that is displayed on the image display 20. As shown in FIG. 9, in the display screen of the image display 20, there are provided a display area 72 of the elastic image data 70 and a display area 74 of the map data 22d indicating the tissue characteristic of the prostate gland.

In the display area 72 for the elastic image 70, the device control interface 5 displays an arrow 78 that is a mark (e.g., a mouse cursor) for setting the area of interest 75 in the elastic image 70. The device control interface 50 accepts an operation to set the area of interest 75 having a shape desired by the laboratory personnel who moves the arrow 78, and displays the area of interest on the elastic image 70. In addition, the device control interface 50 directs the elasticity data arithmetic unit 19 to compute a mean value of the elasticity data within the area of interest 75, and shows a numeric value (92 kPa in FIG. 9) as a result of the computation by displaying the arrow 80 indicating the value, on the display of the discrimination map data 22d in the display area 74. The numerical value of the mean value is displayed also in the display area 76. Alternatively, as shown in FIG. 10, the mean value may be displayed as a numeric value in proximity to the area of interest 75. In addition to the mean value, it is further possible that a deviation value of the elasticity data within the area of interest 75 is computed, and a result of the computation is displayed in proximity to the area of interest 75.

In addition, a table indicating association among the elasticity data (elastic modulus, in this case), a probability (%) indicating the possibility of lesion, and the lesion name, may be previously stored in a memory within the elasticity data arithmetic unit 19. Accordingly, it is possible to display in the area 76, the probability indicating the possibility of lesion, and the name of the lesion, which are associated with the mean value of the elasticity data in the area of interest 75.

Accordingly, the laboratory personnel is allowed to easily figure out the correspondence between the image and the elastic modulus, and also allowed to see a display showing the name of lesion and the probability of the lesion, which are stored as data in the ultrasonic diagnostic apparatus. Therefore, the laboratory personnel is provided with information that assists his or her judgment.

In addition, when the probe 10 is moved manually and vertically to bring pressure on the test object 1, the position of the tissue is changed in accordance with the pressure. Therefore, the area of interest 75 may be displayed in such a manner as following the change (tracking). Specifically, a displacement of the tissue is detected by the displacement measuring unit 17, and a detection result is received by the device control interface 50. Then, the display of the area of interest 75 is moved, whereby the area of interest can be moved along the displacement of the tissue. In this case, for example, a mean value of the elasticity data corresponding to each pixel of the area of interest 75 is updated in real time, and the updated mean value may be displayed in proximity to the area of interest 75 or in the area 76.

It is further possible to configure such that multiple areas of interest R1 and R2 can be set simultaneously. By way of example, as shown in FIG. 10, the device control interface 50 accepts from the laboratory personnel, a setting of the area of interest 75 as the first area of interest R1, and accepts from the laboratory personnel, a setting of the area of interest 84 as the second area of interest R2. In the case above, in displaying the discrimination map data for prostate gland 22d, it is possible to display an arrow 80 indicating a hue corresponding to the average of elasticity data (e.g., 92 kPa) of the area of interest 75, and an arrow 82 indicating a hue corresponding to the elasticity data (e.g., 47 kPa) of the area of interest 84.

According to the display operation and the user interface as shown in FIG. 9 and FIG. 10, the area of interest 75 is set conversationally, or interactively and a display index is visually recognized, thereby allowing the tissue characteristic of the area of interest to be identified objectively and quantitatively. In addition, it is possible to easily figure out the hardness and the hue visually, which are associated with the tissue characteristic of the area of interest. Therefore, usability for the laboratory personnel is enhanced, and the diagnostic efficiency and inspection accuracy can be further improved. In addition, the display mode can be designated or selected by the device control interface 50.

In FIG. 9 and FIG. 10, the configuration to accept the setting of the areas of interest 75 and 84 on the elastic image 70 has been described. However, the configuration is not limited as described above, it is further possible to display a tomographic image (B mode image) in the area 72, and accept a setting of the area of interest on the tomographic image. In the case above, it is possible to set the area of interest, in accordance with the structure of the tissue indicated by the tomographic image. Even when the setting of the area of interest is accepted on the tomographic image, the mean value or the like of the elasticity data is obtained by the computation similar to the case as described above, and such values may be displayed by the arrow 80 or in the area 76.

In the embodiment 5, the configuration has been explained, in which a setting of the area of interest is accepted from the laboratory personnel. However, it is of course possible to automatically set the area of interest, by using a publicly known automatic area setting method. By way of example, it is possible to set a border of the area of interest, on a boundary where the hue on the elastic image is changed, a surrounding part of the region where the brightness is drastically changed on the tomographic image, or the like.

EMBODIMENT 6

Next, as the embodiment 6, an example for displaying a graph 113 that indicates a temporal change of the elasticity data (elastic modulus) in the area of interest 75 will be explained with reference to FIG. 11, in addition to the display example of FIG. 10.

The elasticity data of the tissue of the test object 1 has a nonlinear elastic property, and the data varies nonlinearly by the pressing operation against the test object 1 by the probe 10. Therefore, if the tissue characteristic is identified only by the elasticity data at a certain point of time, it is not possible to completely deny a probability that the elasticity data at the point of time indicates a peculiar value. Furthermore, it may be difficult to determine whether or not a pressing condition is appropriate. In view of the situations above, in the display example as shown in FIG. 11, there is provided an area 114 for displaying the graph 113 indicating a temporal change of the elasticity data, in addition to the display area 72 of the elastic image data 70, and the display area 74 of the discrimination map data 22d indicating the types of tissue and the types of degeneration (characteristic) of prostate gland. The area 114 indicates a temporal change of the mean value of the elasticity data in the areas of interest 75 and 84. In the graph 113, the vertical axis indicates elasticity data (elastic modulus) and the horizontal axis indicates a passage of time. Background area of the graph 113 is separated by color in the vertical axis direction, in the same manner as the discrimination map data 22d.

Change curves 111 and 112 of the elasticity data in the areas of interest 75 and 84 are shown in the graph 113, whereby it is possible to easily figure out whether the change curves 111 and 112 remain in the elasticity data range of one tissue characteristic indicated by the discrimination map data 22d, or enter in the elasticity data range of the type of adjacent tissue or the type of degeneration, depending on the time. Accordingly, the laboratory personnel is allowed to recognize not only the elastic image data at a certain point of time, but also the previous elasticity data before the current time, and thereby identifying the tissue characteristic in a comprehensive manner. It is further possible to determine whether or not the pressing condition is appropriate, according to the amplitudes of the change curves 111 and 112.

It is to be noted that the data displayed in the graph 113 is not limited to one type of elasticity data (elastic modulus), but other elasticity data, such as viscoelasticity ratio, distortion amount, viscosity, amount of displacement, a stress, Poisson's ratio, and the like, may be displayed together. It is further possible to compute and display a parameter and the like, indicating a non-linear property of the viscoelasticity ratio and elastic modulus.

It is further possible to display in the graph 113, a graph indicating the rate of change of the elasticity data along with a passage of time.

In the graph 113 as shown in FIG. 11, the background area is separated by color in association with the display of the discrimination map data 22*d*. However, it is further possible to separate the change curves 111 and 112 themselves by color.

EMBODIMENT 7

As the embodiment 7, discrimination map data for prostate tissue 22*e* and an image display example will be explained with reference to FIG. 12(*a*) to FIG. 12(*d*) for evaluating an effect of treatment by HIFU (high-intensity focused ultrasound).

The treatment by HIFU is a method that emits strong ultrasonic waves from the probe for treatment, and focuses highly intensive ultrasonic waves into a small area. The temperature at the focal point becomes high, such as 60 to 90° C., and a carcinomatous lesion exposed to this high temperature may be destroyed and killed. The small focal point of the HIFU is gradually moved within the prostate gland, and the treatment is performed by irradiating the entire cancer tissue. Since the tissue is hardened by thermal degeneration, it is possible to confirm by the image whether the treatment is performed uniformly on the entire area of the cancer tissue, by using the discrimination map data 22*e* that is partitioned by degree of hardness, in such a manner as associated with the level of treatment effect.

Specifically, the discrimination map data 22*e* as shown in FIG. 12(*a*), the color of light-blue is assigned to the range of elastic modulus (0 to around 80 kPa), which corresponds to a benign denatured tissue (prostatic hypertrophy) and a non-denatured tissue of prostate gland (anterior part of prostate and posterior part of prostate), and the color of red is assigned to the range of elastic modulus (80 to 115 kPa) corresponding to a malignant degeneration (prostatic cancer). The range of the elastic modulus having the color of red indicates an area where no HIFU treatment has been provided, or no thermal degeneration has occurred even after the HIFU treatment (therapeutic effect 0%). Furthermore, the color of yellow is assigned to the elastic modulus range (115 to 130 kPa) indicating that a predetermined thermal degeneration has occurred by the HIFU treatment and the area is hardened to a predetermined value, and the color of green is assigned to the elastic modulus range (130 kPa and more) indicating that a sufficient thermal degeneration is generated, and the area is hardened equal to or more than the predetermined value.

When the discrimination map data 22*e* is used, as shown in FIG. 12(*b*), the elastic image data 121 of the display area 70 before the treatment shows the area 122 of the prostatic cancer in red, similar to the case of FIG. 9. It is figured out that the elastic image data 121 after fifteen times of the irradiation of HIFU to the area 122 shows a sufficient thermal degeneration being generated in most part, and the area is changed to green 123 as shown in FIG. 12(*c*). However, in a part, such sufficient thermal degeneration is not generated and the area is yellow 124. Therefore, if the HIFU irradiation is applied to the yellow area 124, as shown in FIG. 12(*d*), then the yellow area 124 is changed to the green area 123, and it is figured out that sufficient thermal degeneration has occurred.

In the HIFU irradiation apparatus, it is possible to set a position for irradiation, but a degree of the thermal degeneration at that position cannot be known. The ultrasonic diagnostic apparatus having the discrimination map data 22*e* according to the present embodiment is used together with the HIFU irradiation apparatus, whereby it is possible to figure out clearly an area where the thermal degeneration is insufficient by the hue of the image. Therefore, a reliable treatment can be provided.

It is to be noted here that in embodiment 7, the HIFU has been explained as an example. However, the present invention is not only limited to this example but also applied to another treatment method such as RFA (percutaneous radiofrequency ablation), and Cryotherapy that rapidly cools a cancer tissue for treatment. In such cases above, the elastic modulus areas having the colors of yellow and green in the discrimination map data 22*e* are set appropriately for respective therapies.

EMBODIMENT 8

As the embodiment 8, discrimination map data for prostate tissue 22*f* and an image display example will be explained with reference to FIG. 13(*a*) to FIG. 13(*d*) for evaluating a hormone therapy for prostatic cancer. The hormone therapy for prostatic cancer shows a feature that when there appears a therapeutic effect, a cancer tissue is denatured and becomes softened. By using the discrimination map data 22*f* that is separated by a degree of hardness in association with the therapeutic effect level, it is possible to check by the image whether or not the therapeutic effect is produced.

Specifically, in the discrimination map data 22*f* as shown in FIG. 13(*a*), the color of red is assigned to the range of elastic modulus (equal to or more than 80 kPa) corresponding to the prostatic cancer, the color of yellow is assigned to the range of elastic modulus that is a little softer (70 to 80 kPa), and the color of green is assigned to the range of elastic modulus that is softer than a normal tissue (not more than 70 kPa).

When this discrimination map data 22*f* is used, in the image data 131 in the display area 72, the red area before starting the therapy indicates the hardness of the prostatic cancer, and an area of interest 132 is set to this area. If the area of interest 132 is changed to a yellow area in the image data 131 after the hormone therapy is started, it is figured out that the area becomes softer by a predetermined therapeutic effect (for example, 70% effect). After a continuation of the hormone therapy, if the area of interest 132 is displayed in green in the image data 131, it is figured out that a sufficient therapeutic effect is produced (for example, 100% effect).

As thus described, by using the discrimination map data 22*f*, it is possible to clearly figure out the degree of degeneration according to hues in the image, also in the hormone therapy against the prostatic cancer. Therefore, a therapeutic effect can be easily recognized.

EMBODIMENT 9

The discrimination data maps 22*a* to 22*f* used in the aforementioned embodiments 1 to 8 are maps configured based on the elastic modulus (charts 111 and the like in FIG. 4), in the case where a total distortion amount occurring on a target tissue to be diagnosed, according to a pressing operation by the vertical movement of the probe 10, is within a predetermined range. Here, the total distortion amount (total distortion amount=$\Sigma\epsilon(t)$) is a value that is obtained by accumulating a distortion amount ($\epsilon(t)$) measured before and after a minor pressure, from the state with no pressure (time t=0) to the time t. For example, the total distortion amount being 10% indicates that a ratio of length in a tissue distorted by pressure is 10%, with respect to the length of the particular tissue in the pressing direction in the state that the pressure is zero. By way of example, there is a tissue having a length of 5 cm in the state where the pressure is zero, and if the length becomes 4 cm by the pressure, the total distortion amount is 20%. In the present embodiment, this percentage is described as the total distortion amount.

However, as shown in FIG. 14, when the total distortion amount is different, the elastic modulus (elastic coefficient) varies by tissue. A change rate (gradient of graph) of the elastic modulus with respect to each tissue is different greatly by tissue, and it is known from that the graph showing the elastic modulus of the fiber tissue crosses the graph showing the elastic modulus of the mammary duct cancer. By way of example, when the total distortion amount is 20%, the elastic modulus of the mammary duct cancer (pink) is larger than the elastic modulus of the fiber tissue (green). On the other hand, when the total distortion amount is 10%, the elastic modulus of the fiber tissue (green) is larger than the elastic modulus of the mammary duct cancer (pink).

Therefore, the embodiment 9 has a configuration where multiple discrimination data maps are prepared in association with the total distortion amount, in order to perform highly precise tissue identification, and these maps are stored in the discrimination data map storing unit 122. It is desirable that the discrimination data maps are prepared with respect to each total distortion amount. However, as shown in FIG. 14, it is desirable that at least two types of maps (discrimination data map 22a and discrimination data map 22g having the total distortion amount 10%) are prepared, before and after the crossing between graphs of two different tissues (the elastic modulus graph of fiber tissue and the elastic modulus graph of mammary duct cancer).

After having prepared multiple discrimination data maps 22a and 22g, upon computing the elastic modulus, the total distortion amount is computed simultaneously, and a corresponding discrimination data map 22a or 22g in association with the computed total distortion amount is selected. By using the selected discrimination data map 22a or 22g, identification of tissue is performed in association with the elastic modulus at each point of the elastic image data.

By way of example, as shown in FIG. 15(a), the elastic image data measured with the total distortion amount of 10% is separated by color by using the discrimination data map 22g as shown in FIG. 14. As shown in FIG. 15(b), the elastic image data measured with the total distortion amount of 20% is separated by color by using the discrimination data map 22a as shown in FIG. 14. Accordingly, if a tumor in the area of interest has an elastic modulus 100 kPa when the total distortion amount is 10%, according to the discrimination data map 22g, it is displayed in the color of pink, i.e., being identified as mammary duct cancer, as shown in FIG. 15(a). However, if the area is further pressed and the total distortion amount becomes 20%, as known from the mammary duct cancer graph shown in FIG. 14, the tissue of the mammary duct cancer shows a value of elastic modulus around 330 kPa. Therefore, if the identification is performed still using the discrimination data map 22a with the total distortion amount of 10%, it is displayed in the color of red, resulting in that it may be erroneously identified as an infiltrating duct cancer. However, by using the discrimination data map 22a with the total distortion amount of 20%, a partial tissue with the elastic modulus of 330 kPa is displayed in the color of pink as shown in FIG. 15(b), and it is identified as a mammary duct cancer in the same manner as FIG. 15(a). In other words, the partitioned ranges of elastic modulus are changed in accordance with the total distortion amount, and the discrimination data map associated with this change is used appropriately, whereby the same partial tissue is properly identified, without influenced by the total distortion amount applied to the tissue. It is to be noted that a mean value of the total distortion amount in the area of interest 151 is obtained and used, as a value of the total distortion amount used in selecting the discrimination data map.

As described above, according to the embodiment 9, identification of a tissue can be performed considering that even if the tissue is the same, the elasticity data (elastic modulus) may be changed by the total distortion amount. Therefore, highly precise identification is possible.

In the discrimination data maps as shown in the embodiments 1 to 9, the elasticity data ranges in association with the types of tissue and the types of degeneration (characteristics) are predetermined values. However, it is further possible to configure such that the elasticity data range is obtained by computation based on the elasticity data and the like being actually measured. For example, the following configuration is possible; the elasticity data items of a denatured partial tissue and a non-denatured partial tissue, which are obtained by taking an image of multiple test objects, are stored cumulatively in a storage area such as a partial area in the memory circuit 46. Then, the multiple elasticity data items stored in the storage area are statistically processed and the ranges of elasticity data of a partial tissue being denatured and of a partial tissue not denatured are determined. By way of example, when a mean value of the elasticity data of the same partial tissue is assumed as "a" and a standard deviation is assumed as "σ", the values of a±σ, a±2σ, and the like, may be assumed as the range of elasticity data for the tissue.

In the embodiments as described above, it is further possible to store in the cine memory 52, the monochrome tomographic image data or the elastic image data outputted from the switch adder 44, the cine memory 52 being connected to the switch adder 44 and the image display 20. Since the monochrome tomographic image or the elastic image data being stored can be outputted to the image display 20 in response to a control command from the device control interface 50, it is possible to display the monochrome tomographic image and the color elastic image in real time while taking an ultrasonic image. In addition, even after the ultrasonic diagnostic apparatus is stopped, an image can be reproduced and displayed as required. Therefore, the test object 1 can be diagnosed on a case-by-case basis, and a diagnostic efficiency or an inspection precision may be further improved.

The present embodiment has been made considering a situation that a thing that a laboratory personnel needs is not a value of hardness itself on a portion of interest, but a tissue characteristic, such as existence or non-existence of degeneration and a probability of lesion on the portion. In view of such situation, the color information converter circuit 18 applied to the ultrasonic diagnostic apparatus uses the discrimination data map 22, so as to assign the hue information and the monochrome brightness information corresponding to the elasticity data, indicating a tissue characteristic in the area. Accordingly, the color elastic image finally displayed on the image display 20 is an image created directly from the tissue characteristic of a portion of interest. Therefore, by referring to the color elastic image, the tissue characteristic such as existence or non-existence of degeneration in the portion of interest can be promptly identified by the image, and a clinically usable ultrasonic diagnostic apparatus can be implemented. It is to be noted that the color elastic image may be structured by the use of an index value that is correlated with a value of elasticity data, for example, a ratio of distortion between the areas of interest R1 and R2 in FIG. 10.

BRIEF DESCRIPTION OF DRAWINGS

FIG. 2(A) is a perspective view of an ultrasonic probe 10 shown in FIG. 1, and FIG. 2(B) is a perspective view of another configuration of the ultrasonic probe 10 shown in FIG. 1;

FIG. 15(a) is an explanatory diagram showing the elastic image separated by color using the discrimination data map 22g as shown in FIG. 9 when the total distortion amount is 10% in the embodiment 9, and FIG. 15(b) is an explanatory diagram showing the elastic image separated by color using the discrimination data map 22a as shown in FIG. 9 when the total distortion amount is 20% in the embodiment 9.

DENOTATION OF REFERENCE NUMERALS

Figure 1:
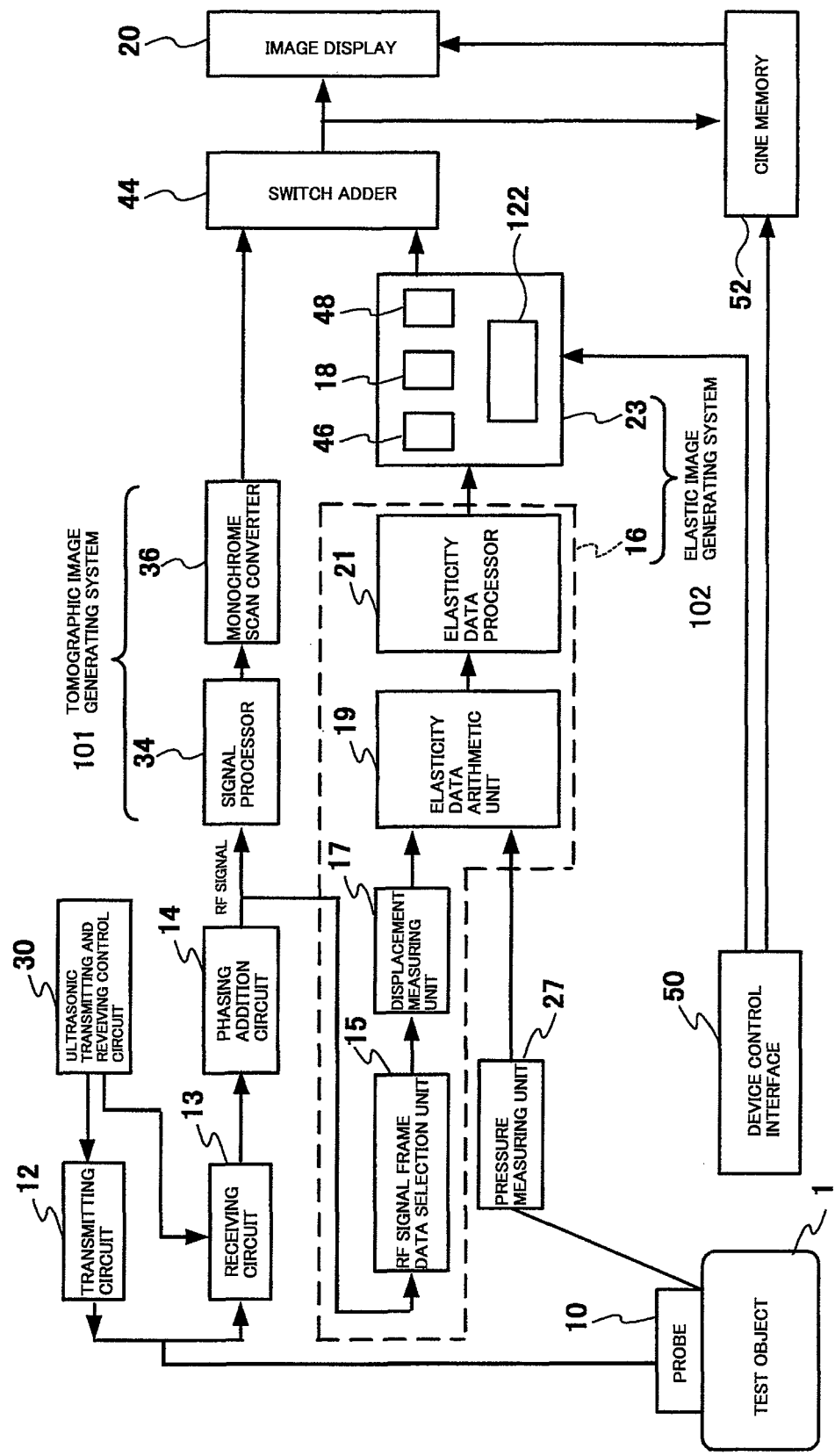
FIG. 1 is a block diagram showing a configuration of an ultrasonic diagnostic apparatus according to one embodiment to which the present invention is applied.
Figure 3:
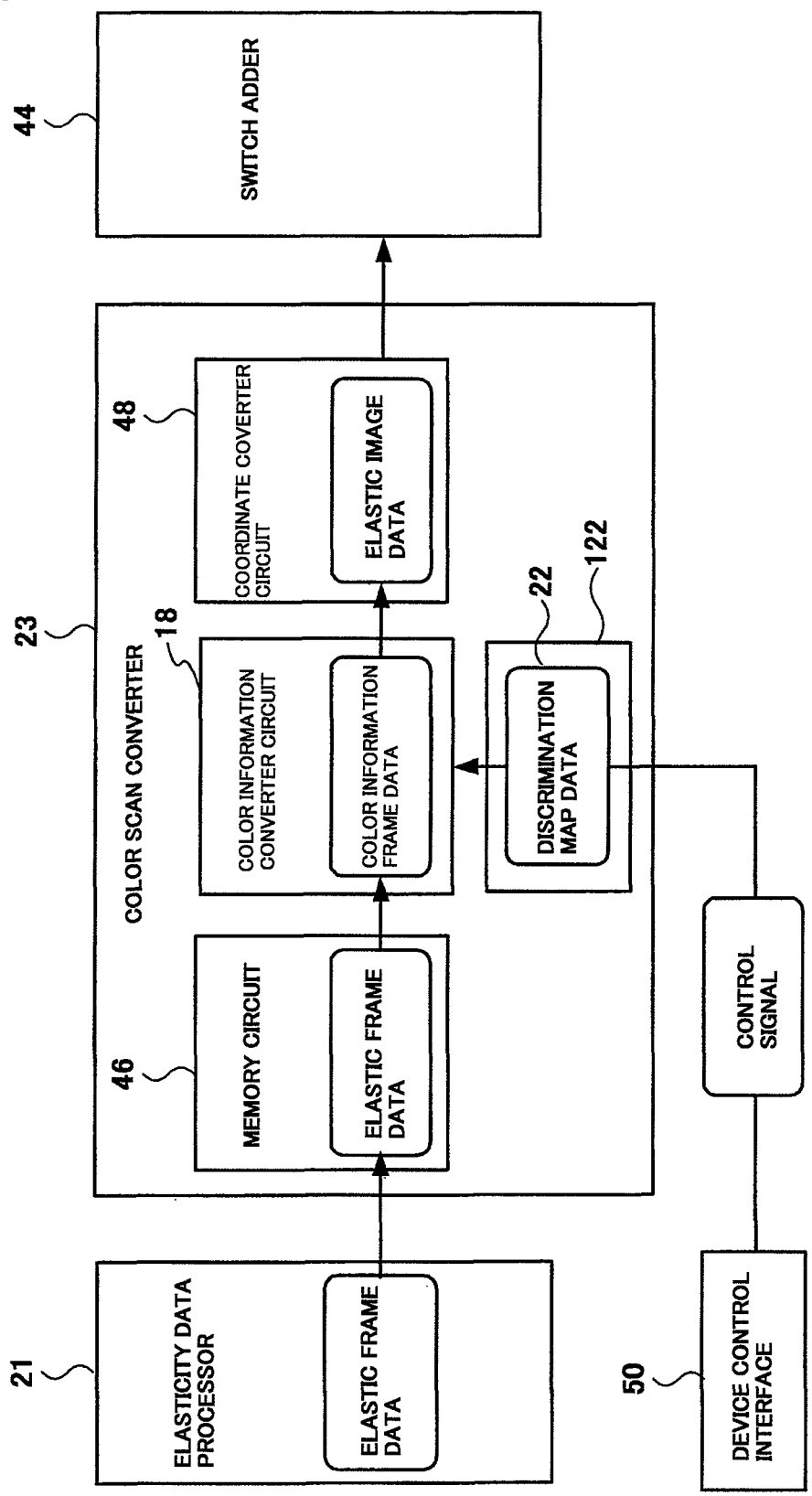
FIG. 3 is a block diagram showing a detailed configuration of the color scan converter shown in FIG. 1.
Figure 4:
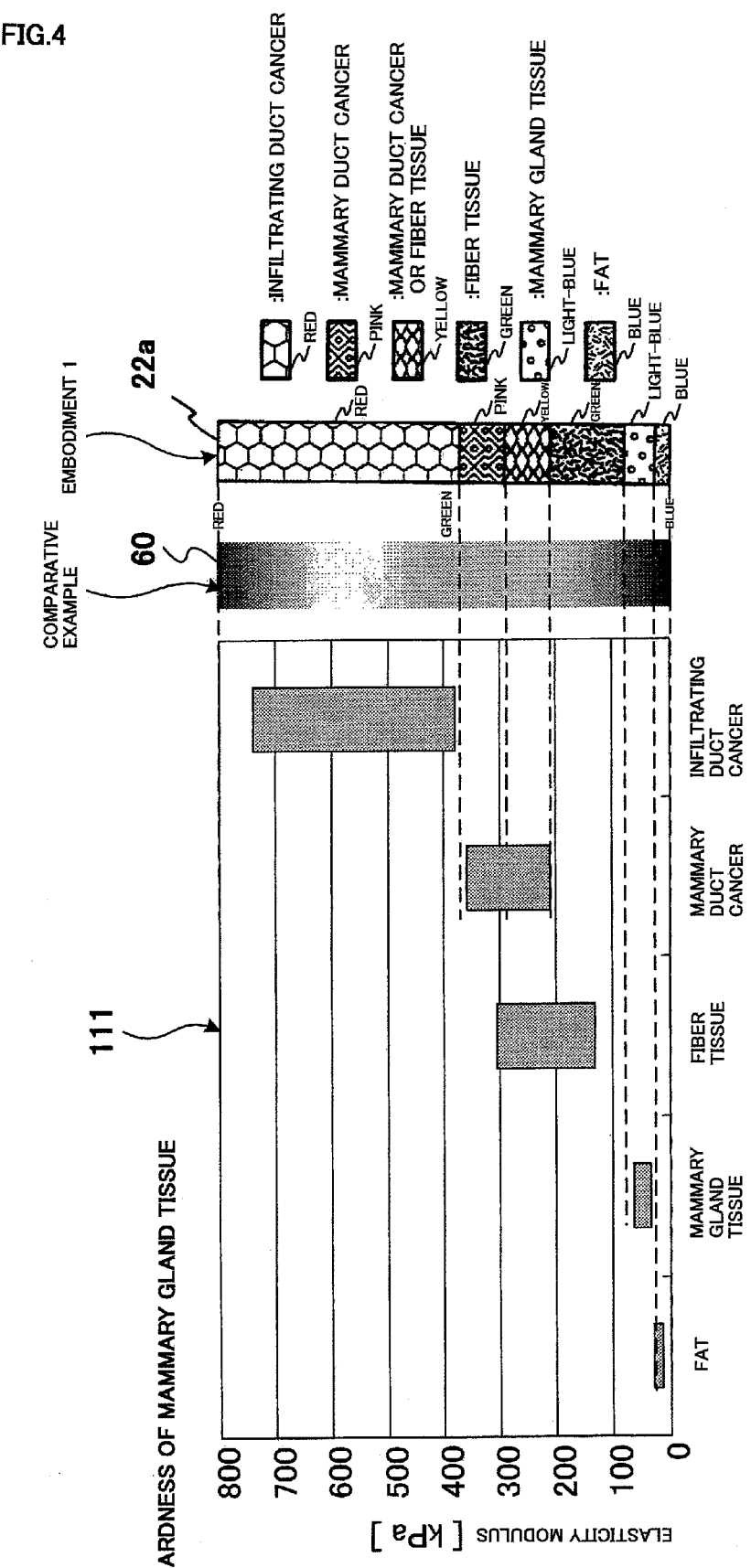
FIG. 4 is an explanatory diagram showing the discrimination map data 22a of the embodiment 1, the color map data 60 of the comparative example, and the graph 111 illustrating a relationship between the mammary gland tissue and the elastic modulus.
Figure 5:
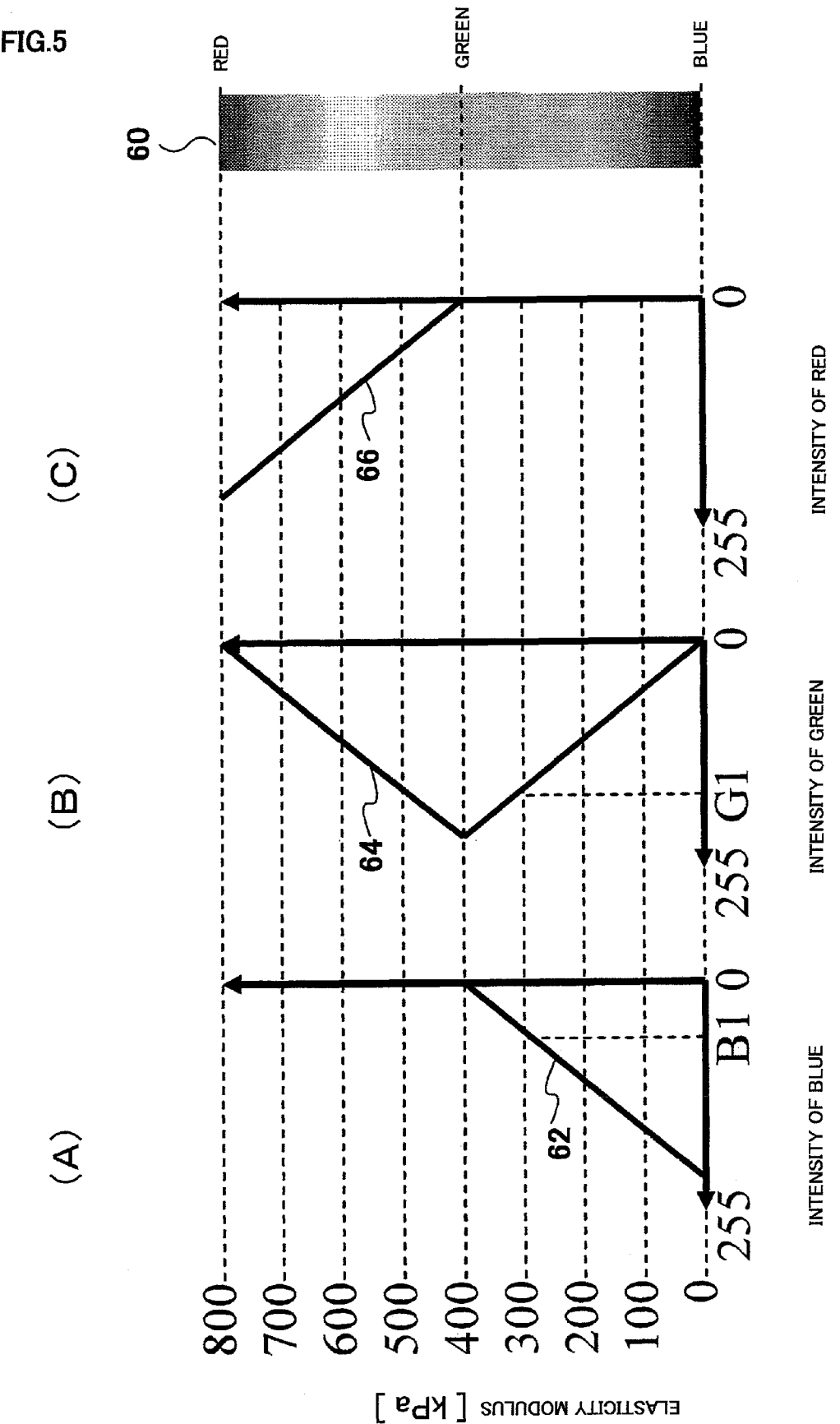
FIG. 5 is an explanatory diagram showing the color map data of the comparative example.
Figure 6:
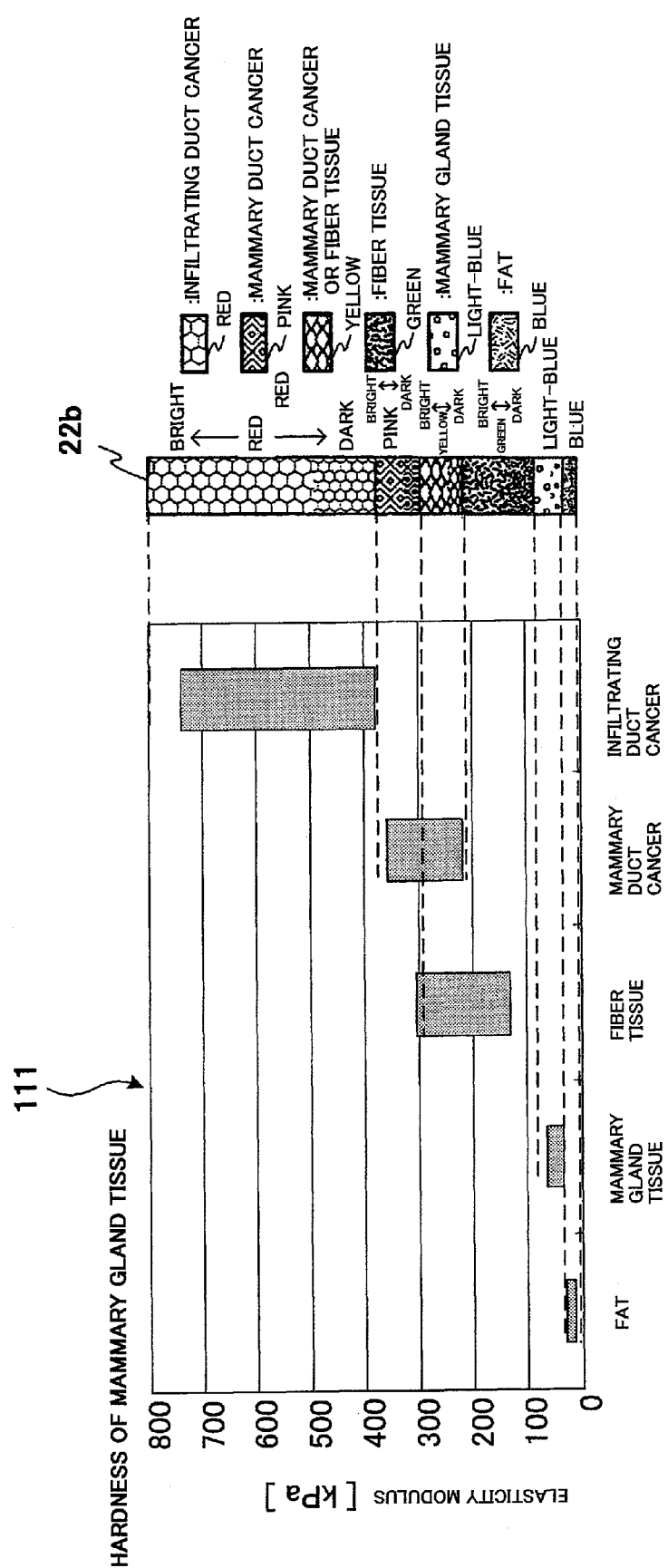
FIG. 6 is an explanatory diagram showing the discrimination map data 22b of the embodiment 2, and the graph 111 illustrating a relationship between the mammary gland tissue and the elastic modulus.
Figure 7:
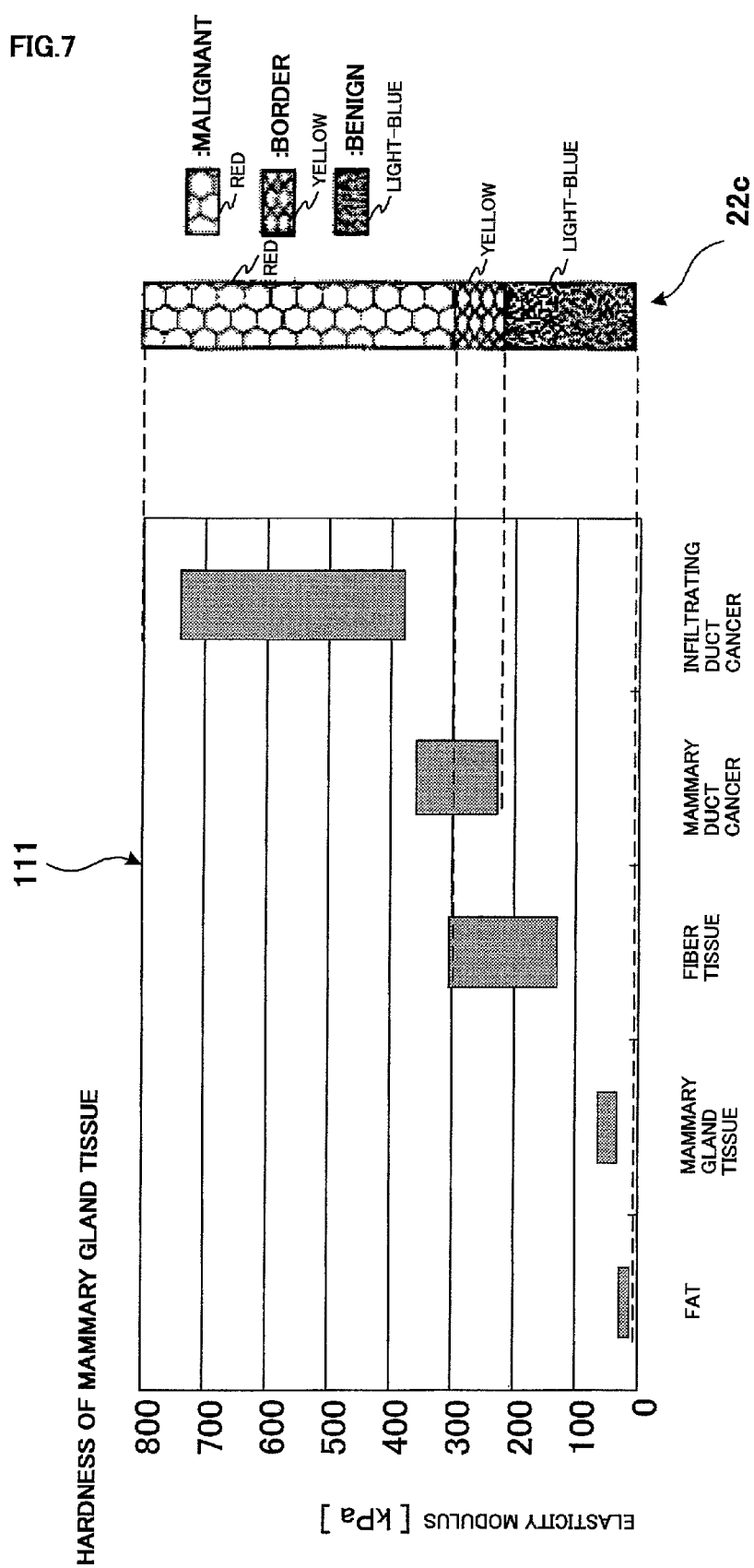
FIG. 7 is an explanatory diagram showing the discrimination map data 22c of the embodiment 3, and the graph 111 illustrating a relationship between the mammary gland tissue and the elastic modulus.
Figure 8:
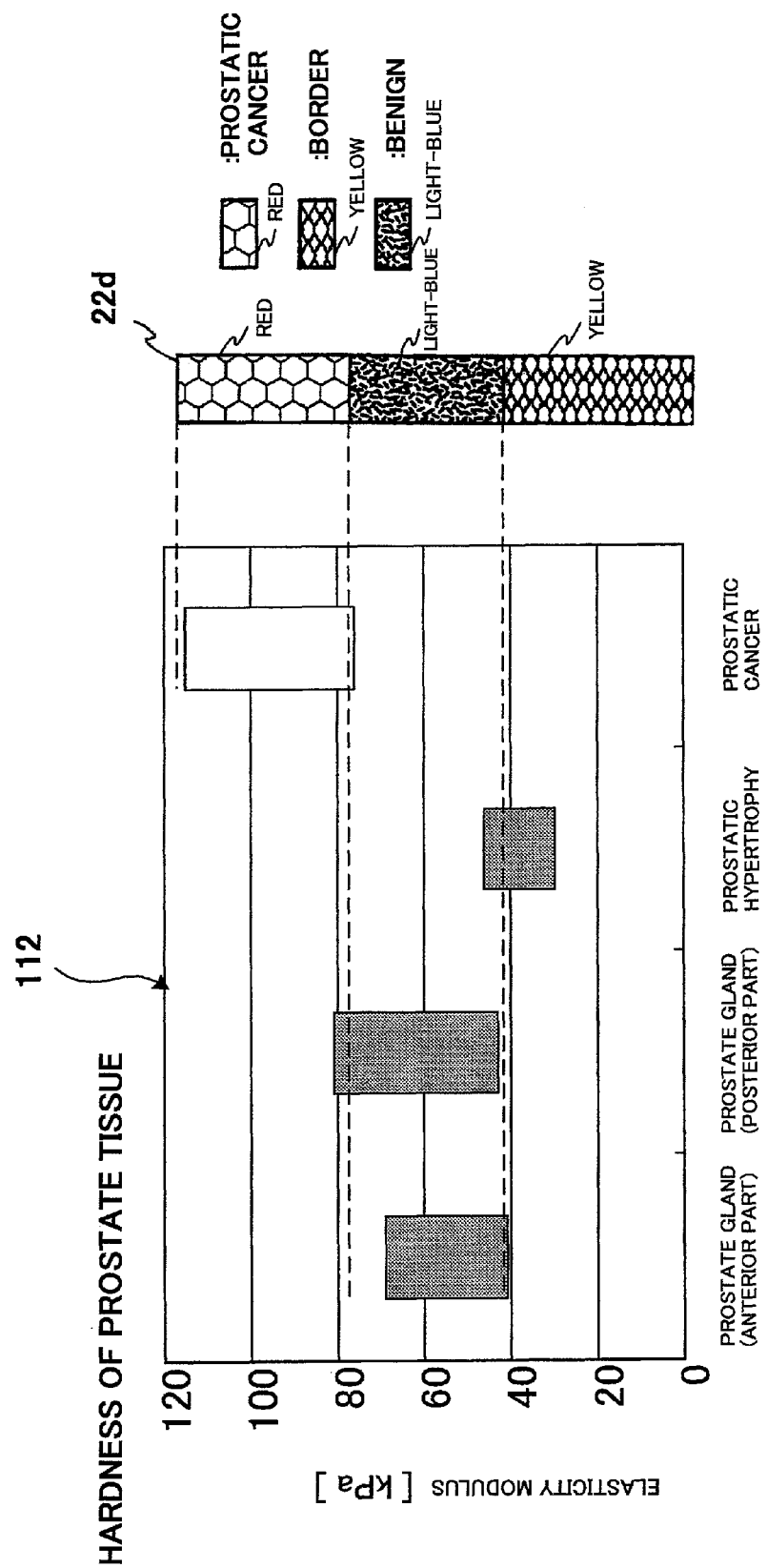
FIG. 8 is an explanatory diagram showing the discrimination map data 22d of the embodiment 4, and the graph 112 illustrating a relationship between the prostate tissue and the elastic modulus.
Figure 9:
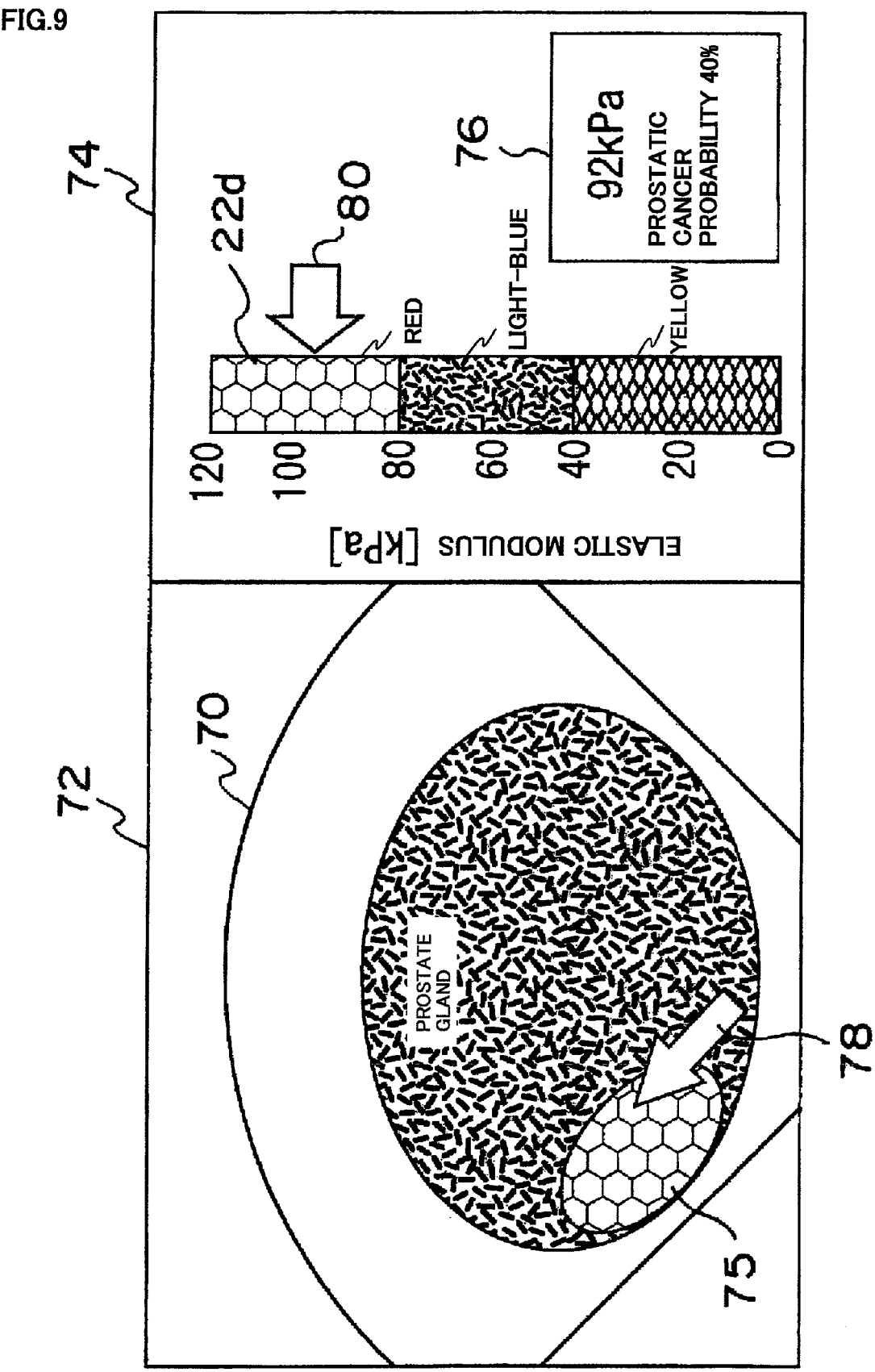
FIG. 9 is an explanatory diagram showing a display example in the image display 20 of the embodiment 5.
Figure 10:
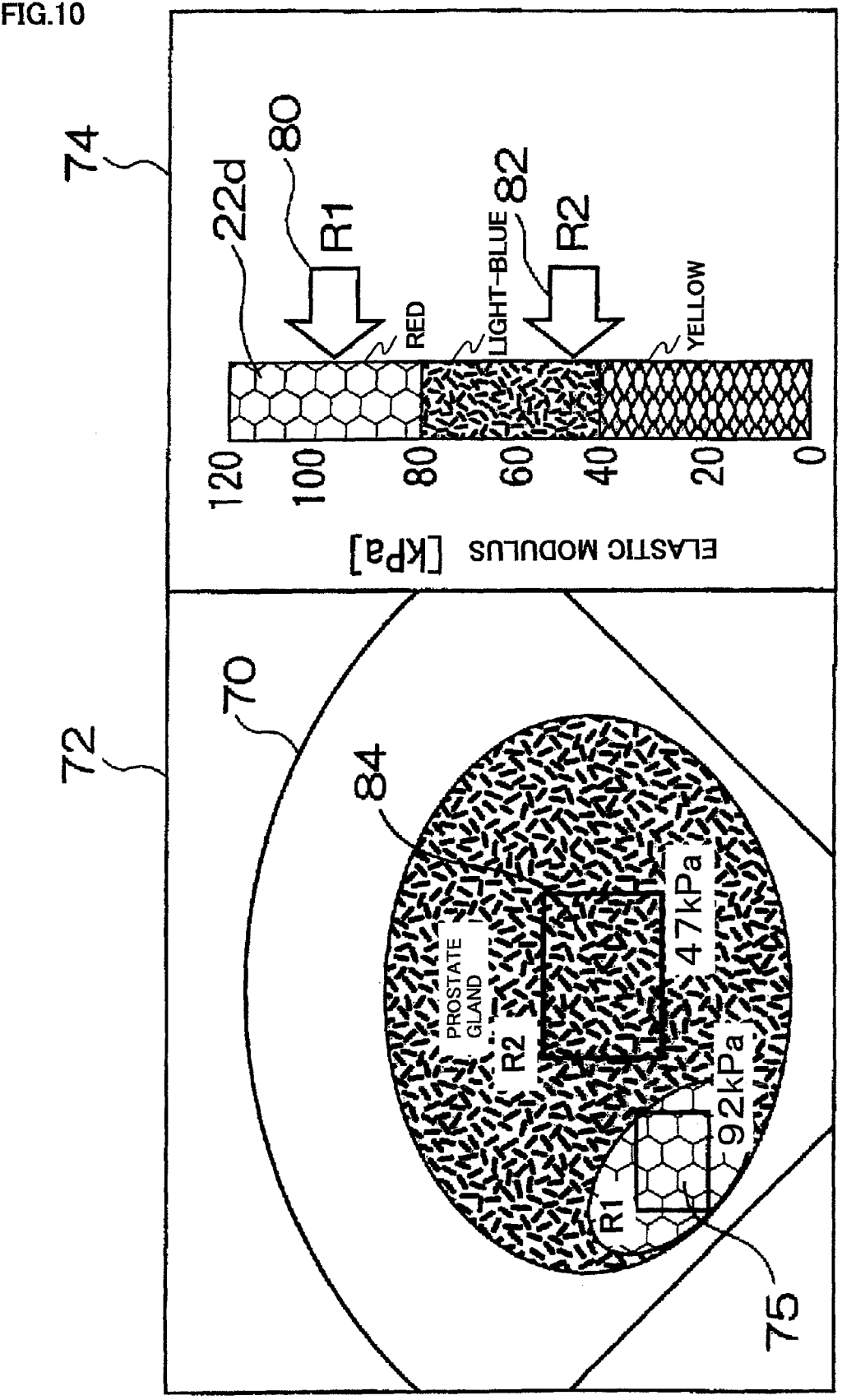
FIG. 10 is an explanatory diagram showing a display example in the image display 20, when the areas of interest are set at two locations in the embodiment 5.
Figure 11:
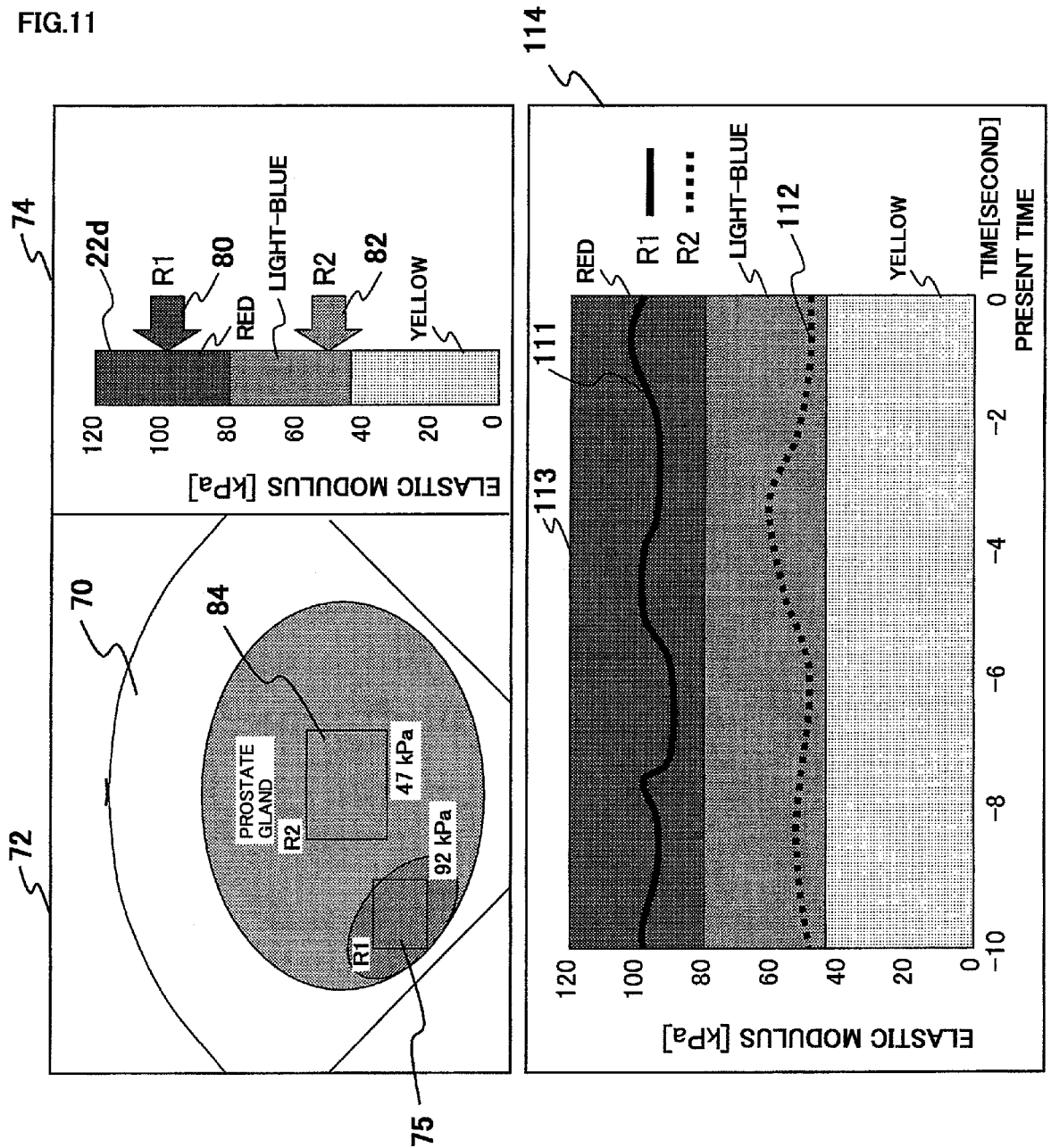
FIG. 11 is an explanatory diagram showing display examples in the image display 20 in the embodiment 6.
Figure 12:
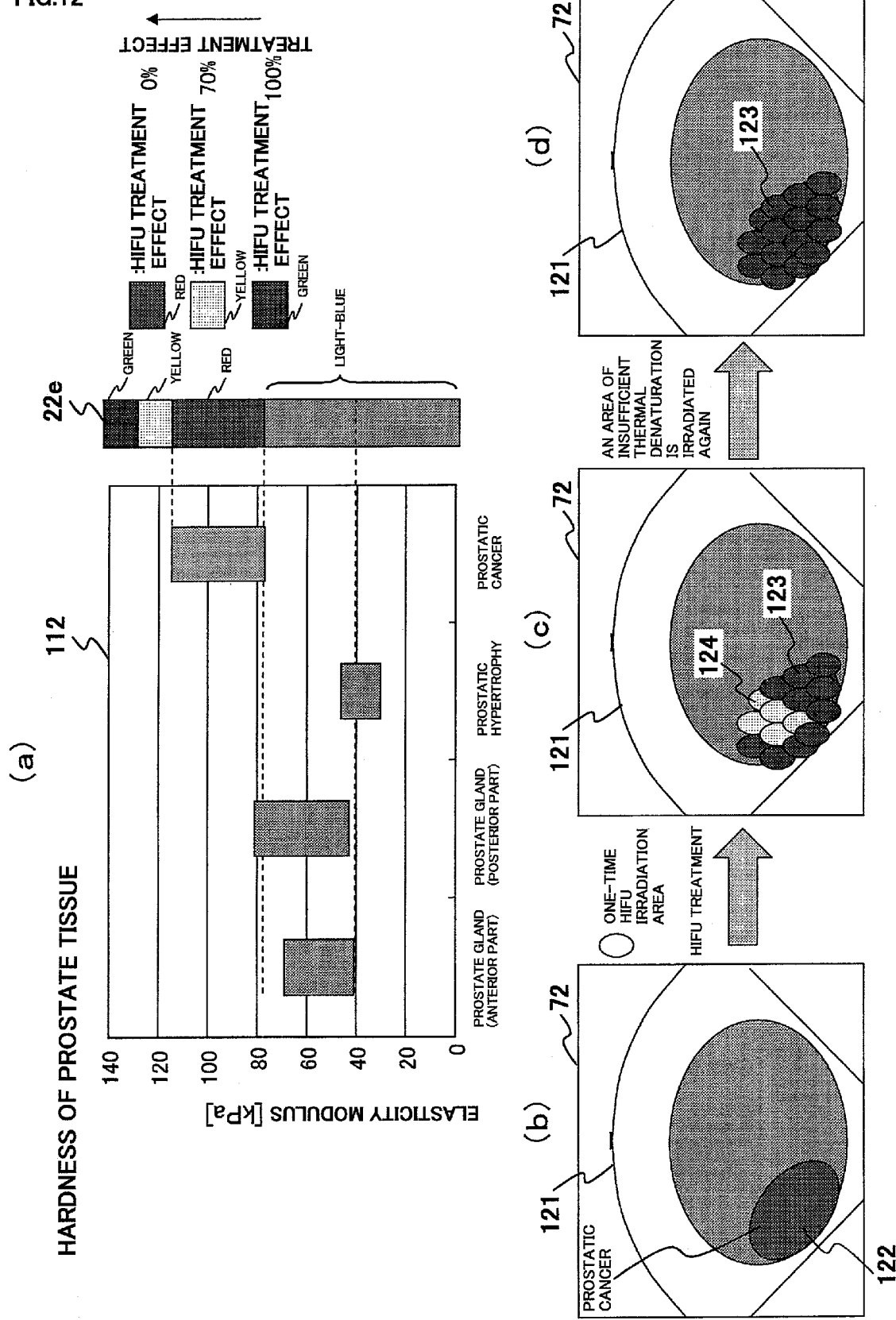
FIG. 12(a) is an explanatory diagram showing the discrimination map data 22d of the embodiment 7, and the graph 112 indicating the relationship between the prostate tissue and the elastic modulus.
FIG. 12(b) to FIG. 12(d) are explanatory diagrams respectively showing display examples, before and after the irradiation of HIFU, and after the re-irradiation of HIFU.
Figure 13:
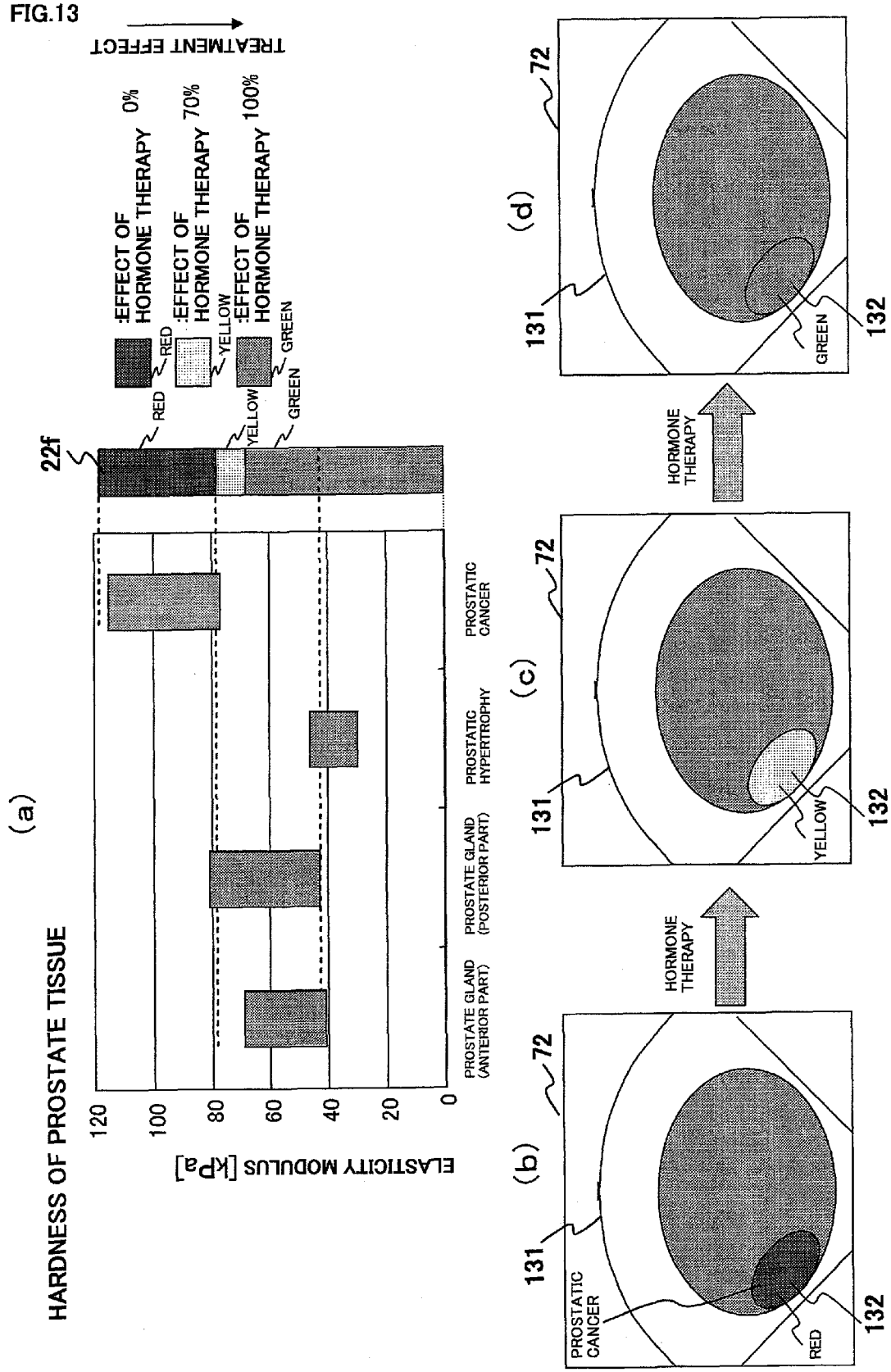
FIG. 13(a) is an explanatory diagram showing the discrimination map data 22d of the embodiment 8, and the graph 112 indicating the relationship between the prostate tissue and the elastic modulus.
FIG. 13(b) to FIG. 13(d) are explanatory diagrams respectively showing display examples, before the hormone therapy, after the hormone therapy is started, and after an effect of the hormone therapy appears.
Figure 14:
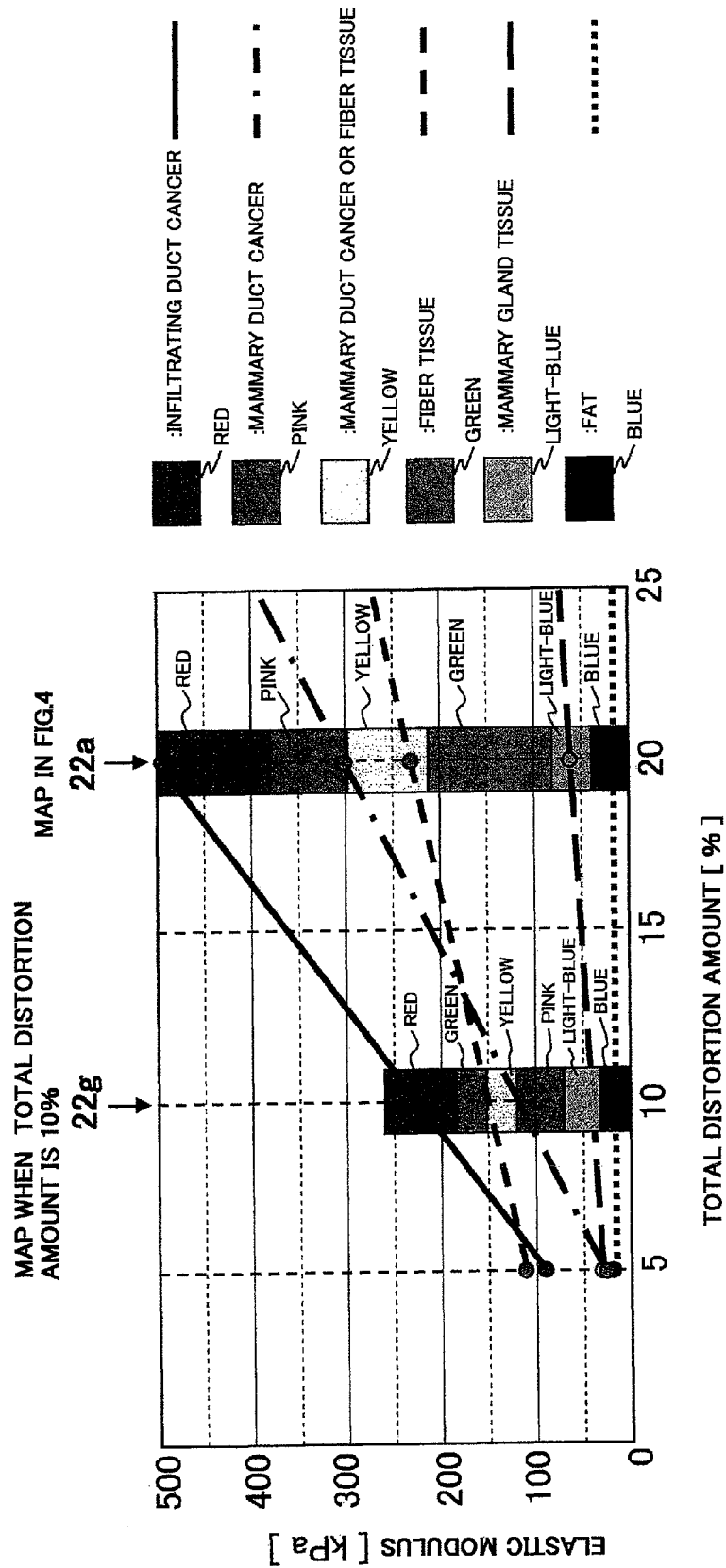
FIG. 14 is a graph showing the discrimination data maps 22a and 22g used in the embodiment 9, and showing that the elastic modulus of the tissue varies according to the total distortion amount.

10 . . . PROBE, 12 . . . TRANSMITTING CIRCUIT, 13 . . . RECEIVING CIRCUIT, 16 . . . ELASTICITY DATA CONFIGURATION UNIT, 18 . . . COLOR INFORMATION CONVERTER CIRCUIT, 20 . . . IMAGE DISPLAY, 23 . . . COLOR SCAN CONVERTER, 44 . . . SWITCH ADDER, 46 . . . MEMORY CIRCUIT, 48 . . . COORDINATE CONVERTER CIRCUIT, 50 . . . DEVICE CONTROL INTERFACE, 52 . . . CINE MEMORY, 101 . . . TOMOGRAPHIC IMAGE GENERATING SYSTEM, 102 . . . ELASTIC IMAGE GENERATING SYSTEM, 122 . . . DISCRIMINATION DATA MAP STORING UNIT

What is claimed is:

1. An ultrasonic diagnostic apparatus comprising:
an ultrasonic probe configured to transmit an ultrasonic wave to, and receive an ultrasonic wave from, a test object,
a computer including at least one processor, to effect operations including:
obtaining elasticity data regarding the test object, based on a received signal of the ultrasonic probe,
generating an elastic image showing a distribution of the elasticity data of the test object,
setting a display mode of the elastic image, in order that different types of tissue of the test object becomes individually identifiable based on a value of the elasticity data,
identifying predetermined degeneration types within one tissue type according to the value of the elasticity data, and setting different display modes corresponding to the degeneration types with one tissue type, and
separating as a different elasticity data range, an area where the elasticity data ranges corresponding to at least two degeneration types are overlapping elasticity data ranges, and imparting different color information to the area.

2. The ultrasonic diagnostic apparatus according to claim 1, wherein,
the color information includes a hue and brightness, and the computer is further configured to effect operations including: changing at least one of the hue and the brightness continuously along the one tissue in a manner corresponding to a degeneration state within the one tissue.

3. The ultrasonic diagnostic apparatus according to claim 2, wherein,
the computer is further configured to effect operations including: imparting the same hue to a denatured area within the one tissue, and changing the brightness of the hue continuously along the one tissue in a manner corresponding to the degeneration state on the denatured area.

4. The ultrasonic diagnostic apparatus according to claim 1, wherein,
the computer is further configured to effect operations including imparting color information as the display mode.

5. The ultrasonic diagnostic apparatus according to claim 1, wherein,
the computer is further configured to effect operations including imparting a pattern as the display mode.

6. The ultrasonic diagnostic apparatus according to claim 1, wherein,
the computer is further configured to effect operations including imparting numerical value information representing an elasticity property, as the display mode.

7. The ultrasonic diagnostic apparatus according to claim 1, wherein,
the computer is further configured to effect operations including dividing a range of the elasticity data according to the degeneration type, and imparting different color information respectively to points in the one tissue, in association with the elasticity data ranges in which the elasticity data item of each of the points is included.

8. The ultrasonic diagnostic apparatus according to claim 7, wherein,
the computer is further configured to effect operations including imparting the color information in such a manner that the color information discretely varies on the border between the elasticity data ranges.

9. The ultrasonic diagnostic apparatus according to claim 7, wherein,
the computer is further configured to effect operations including controlling imparting of the color information in such a manner that the same color information is assigned to the same degeneration type within the one tissue.

10. The ultrasonic diagnostic apparatus according to claim 9, wherein,
the computer is further configured to effect operations including preparing multiple types of elasticity data ranges in advance, and selecting the type of the elasticity data ranges so that the same color information is assigned to the same degeneration type.

11. The ultrasonic diagnostic apparatus according to claim 7, further comprising,
a memory configured to store a value of the elasticity data for each of the degeneration types, with respect to each test object, wherein,
the computer is further configured to effect operations including defining the elasticity data range for each of the degeneration types, based on the elasticity data, more than one, being stored in the memory.

12. The ultrasonic diagnostic apparatus according to claim 1, wherein,
the degeneration types includes at least one of: a cancer tissue, a thermally hardened tissue, a fibrous tissue, a tissue hardened by cooling, and a tissue softened by hormone therapy.

13. The ultrasonic diagnostic apparatus according to claim 7, further comprising:
a storage configured to store a map in which the elasticity data range is associated with the color information, and wherein
the computer is further configured to effect operations including imparting the color information to each point of the image according to the map.

14. The ultrasonic diagnostic apparatus according to claim 13, wherein,
the storage stores at least one map for each diagnostic part of the test object, and wherein
the computer is further configured to effect operations including selecting and using the map according to the diagnostic part of the test object.

15. The ultrasonic diagnostic apparatus according to claim 7, wherein the computer is further configured to effect operations including to display the elastic image in a form of a color bar.

16. The ultrasonic diagnostic apparatus according to claim 4, wherein,
the color information includes at least one of a hue and brightness.

17. The ultrasonic diagnostic apparatus according to claim 16, wherein,
the computer is further configured to effect operations including imparting different brightness according to the value of elasticity data, as to a point having the elasticity data within the elasticity data range to which the same hue is imparted.

18. The ultrasonic diagnostic apparatus according to claim 1, wherein
the elasticity data is at least one of: elastic modulus, viscoelasticity ratio, distortion amount, viscosity, an amount of displacement, a stress, and Poisson's ratio.

19. The ultrasonic diagnostic apparatus according to claim 15, wherein the computer is further configured to effect operations including accepting a setting of an area of interest against the elastic image that is displayed, to obtain statistical information about the elasticity data of each point within the area of interest, and displaying the statistical information in such a manner as associated with the elasticity data range on the color bar, or with the area of interest.

20. The ultrasonic diagnostic apparatus according to claim 19, wherein
the computer is further configured to effect operations including displaying a background area being separated by color just like the color bar on the displayer, and displaying a graph representing a temporal change of a mean value in such a manner as superimposing on the background area.

21. An ultrasonic diagnostic apparatus comprising:
an ultrasonic probe configured to transmit an ultrasonic wave to, and receive an ultrasonic wave from, a test object,
a computer including at least one processor to effect operations including:
obtaining elasticity data regarding the test object, based on a received signal of the ultrasonic probe,
generating an elastic image showing a distribution of the elasticity data of the test object
setting a display mode of the elastic image, in order that different types of tissue of the test object become individually identifiable based on a value of the elasticity data,
setting different display modes within one tissue of the different types of tissues, in a manner corresponding to the value of the elasticity data thereof, and to impart a same hue to the one tissue, and to change the brightness of the hue continuously along the one tissue type in a manner corresponding to variation of the elasticity data within the one tissue, and
identifying predetermined degeneration types within one tissue type according to the value of the elasticity data, assigning different hues to the different types of tissues respectively, and changing the brightness of the hue in each type of tissue in a manner corresponding to a degeneration state as reflected by variation of the elasticity data within the tissue, and
separating as a different elasticity data range, an area where the elasticity data ranges corresponding to at least two degeneration types are overlapping elasticity data ranges, and imparting different color information to the area.

22. An ultrasonic diagnostic apparatus comprising:
an ultrasonic probe configured to transmit an ultrasonic wave to, and receive an ultrasonic wave from, a test object,
a computer including at least one processor to effect operations including:
obtaining elasticity data regarding the test object, based on a received signal of the ultrasonic probe,
generating an elastic image showing a distribution of the elasticity data of the test object, setting a display mode of the elastic image, in order that different types of tissue of the test object becomes individually identifiable based on a value of the elasticity data, setting different display modes within one tissue type of the different types of tissues, in a manner corresponding to the value of the elasticity data thereof, and imparting a same hue to the one tissue type, and changing the brightness of the hue continuously along the one tissue type in a manner corresponding to variation of the elasticity data within the one tissue type, assigning different hues to the different types of tissues respectively, and changing the brightness of the hue in each type of tissue in a manner corresponding to the variation of the elasticity data within the tissue, identifying predetermined degeneration types within one tissue type according to the value of the elasticity data, setting different display modes corresponding to the degeneration types with one tissue type, and imparting color information differentiated by a degeneration state within one tissue type, and separating as a different elasticity data range, an area where the elasticity data ranges corresponding to at least two degeneration types are overlapping elasticity data ranges, and imparting different color information to the area.

23. The ultrasonic diagnostic apparatus according to claim 1, further comprising a storage that stores predetermined discrimination map data assigning color information to the ranges of the elasticity data corresponding to types of tissues and types of degeneration, wherein the computer is further configured to effect operations including setting different display modes corresponding to the degeneration types with one tissue type using the discrimination map data.

24. The ultrasonic diagnostic apparatus according to claim 1, wherein the computer is further configured to effect operations including assigning to an area where at least two degeneration types are overlapping elasticity data ranges, a color different from colors assigned to the degeneration types.

* * * * *